(12) United States Patent
Helms et al.

(10) Patent No.: US 11,260,103 B2
(45) Date of Patent: *Mar. 1, 2022

(54) COMPOSITIONS AND METHODS FOR DELIVERING LYOPHILIC AGENTS TO DENTAL PULP AND FOR ENHANCING DENTIN PRODUCTION

(71) Applicant: The Board of Trustees of the Leland Stanford Junior University, Stanford, CA (US)

(72) Inventors: Jill Helms, Stanford, CA (US); Daniel L. Hunter, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 191 days.

This patent is subject to a terminal disclaimer.

(21) Appl. No.: 16/669,340

(22) Filed: Oct. 30, 2019

(65) Prior Publication Data
US 2020/0046801 A1 Feb. 13, 2020

Related U.S. Application Data

(63) Continuation of application No. 15/539,489, filed as application No. PCT/US2015/067683 on Dec. 28, 2015, now Pat. No. 10,512,668.

(60) Provisional application No. 62/097,502, filed on Dec. 29, 2014.

(51) Int. Cl.
| | |
|---|---|
| A61K 38/00 | (2006.01) |
| A61K 38/17 | (2006.01) |
| A61K 6/58 | (2020.01) |
| A61K 6/69 | (2020.01) |
| A61K 9/00 | (2006.01) |
| A61K 9/08 | (2006.01) |
| A61K 9/127 | (2006.01) |
| A61K 38/18 | (2006.01) |

(52) U.S. Cl.
CPC ............... *A61K 38/17* (2013.01); *A61K 6/58* (2020.01); *A61K 6/69* (2020.01); *A61K 9/0019* (2013.01); *A61K 9/08* (2013.01); *A61K 9/127* (2013.01); *A61K 38/18* (2013.01)

(58) Field of Classification Search
None
See application file for complete search history.

(56) References Cited

U.S. PATENT DOCUMENTS
| | | |
|---|---|---|
| 8,809,272 B2 | 8/2014 | Helms |
| 2008/0226707 A1 | 9/2008 | Helm et al. |
| 2012/0115788 A1 | 5/2012 | Helms |
| 2012/0231091 A1 | 9/2012 | Tamashiro et al. |
| 2012/0329790 A1 | 12/2012 | Markowitz |
| 2014/0371151 A1 | 12/2014 | Helms |

FOREIGN PATENT DOCUMENTS
| | | |
|---|---|---|
| WO | 2006/100071 A1 | 9/2006 |
| WO | 2009/055609 A1 | 4/2009 |
| WO | 2009/100268 A2 | 8/2009 |
| WO | 2009/100283 A2 | 8/2009 |
| WO | 2012122081 A2 | 9/2012 |
| WO | 2014153548 A1 | 9/2014 |

OTHER PUBLICATIONS

Han et al., "β-Catenin Enhances Odontoblastic Differentiation of Dental Pulp Cells through Activation of Runx2", PLoS One, Feb. 10, 2014, pp. 1-10, vol. 9, Issue 2, e88890, PLoS One, San Francisco, CA.
Mao et al. "Stem Cells in the Face: Tooth Regeneration and Beyond", Cell Stem Cell, Sep. 7, 2012, pp. 291-301, vol. 11, No. 3, Elsevier, Amsterdam, Netherlands.
Arioka et al., "Acceleration of bone regeneration by local application of lithium: Wnt signal-mediated osteoblastogenesis and Wnt signal-independent suppression of osteoclastogenesis", Biochem Pharmacol., Aug. 15, 2014, pp. 397-405, vol. 90, Issue 4, Elsevier, Amsterdam, Netherlands.
Zhang et al., "Canonical Wnt signaling acts synergistically on BMP9-induced osteo/odontoblastic differentiation of stem cells of dental apical papilla (SCAPs)", Biomaterials, Jan. 2015, pp. 145-154, (39), Elsevier, Amsterdam, Netherlands.
Zhang et al. "Making a tooth: growth factors, transcription factors, and stem cells," Cell Research, May 1, 2005, pp. 301-316, vol. 15, No. 5, Nature, London, United Kingdom.
Minear et al., "Wnt Proteins Promote Bone Regeneration", Sci Transl Med., Apr. 28, 2010, pp. 1-9, 2(29), American Association for the Advancement of Science, Washington DC.
Moon et al., "WNT and bold beta-catenin signalling: diseases and therapies", Nat Rev Genet., Sep. 2004, pp. 691-701, 5(9), Nature Publishing Group, London, United Kingdom.
Dhamdhere et al., "Drugging a Stem Cell Compartment Using Wnt3a Protein as a Therapeutic", PLoS One, Jan. 6, 2014, 9(1), PLoS One, San Francisco, CA. pp. 1-11.
Zhao et al., "Chapter 17 Controlling the In Vivo Activity of Wnt Liposomes", Methods Enzymol., 2009, pp. 331-347, vol. 465, Elsevier, Amsterdam, Netherlands.
Lim et al. "Wnt signaling regulates pulp volume and dentin thickness," J Bone Miner Res., Apr. 1, 2014, pp. 392-901, vol. 29, No. 4, Wiley, Hoboken, NJ.

*Primary Examiner* — Jeanette M Lieb
(74) *Attorney, Agent, or Firm* — Pamela J. Sherwood; Bozicevic, Field & Francis LLP

(57) ABSTRACT

Methods and compositions are provided for enhancing dentin production, and for delivering a lipophilic agent to pulp tissue of a tooth of an individual. In some cases, a subject method includes a step of administering to the pulp of a tooth of an individual, a Wnt stimulating composition that includes a Wnt stimulator agent, at a dose sufficient to enhance the production of dentin by the pulp. In some cases, a subject method includes a step of contacting exposed dentin of a tooth with a composition that includes a lipophilic agent inserted in the non-aqueous phase of a lipid structure (e.g., whereby the lipophilic agent penetrates the dentin to the underlying pulp tissue). Kits are also provided for practicing the methods of the disclosure.

20 Claims, 17 Drawing Sheets
(17 of 17 Drawing Sheet(s) Filed in Color)
Specification includes a Sequence Listing.

Pentachrome

Nestin

DSP

$Axin2^{LacZ/+}$ X-gal

$Axin2^{CreERT2/+};R26R^{mTmG/+}$

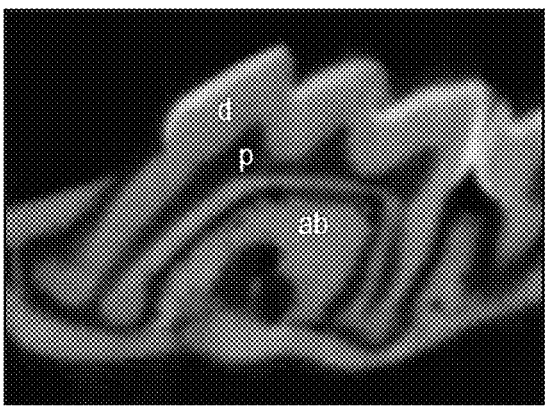 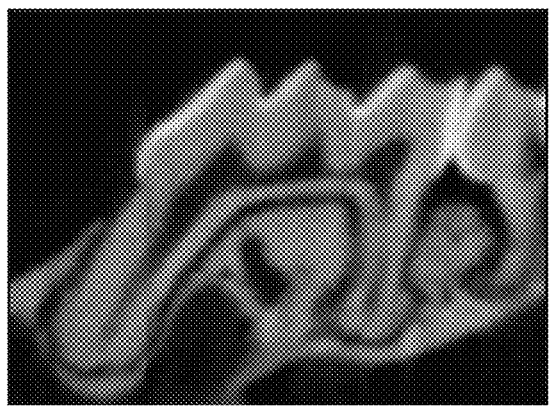
FIG. 2A      FIG. 2B
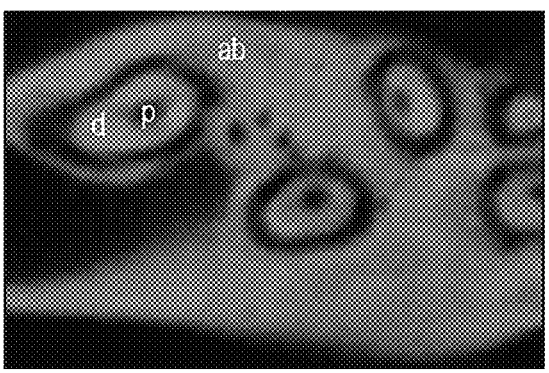 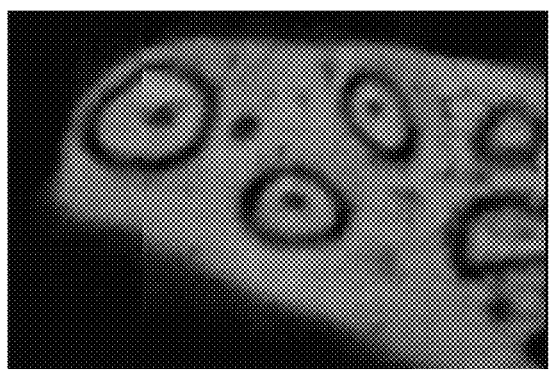
FIG. 2C      FIG. 2D
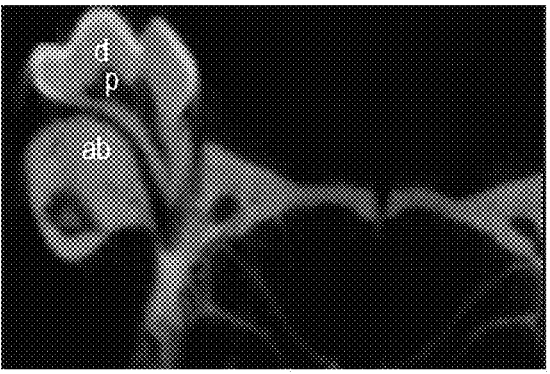 
FIG. 2E      FIG. 2F
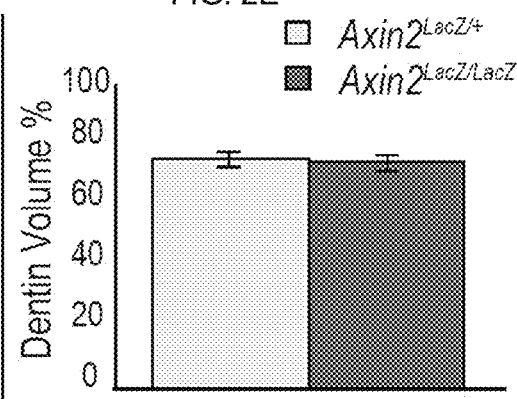 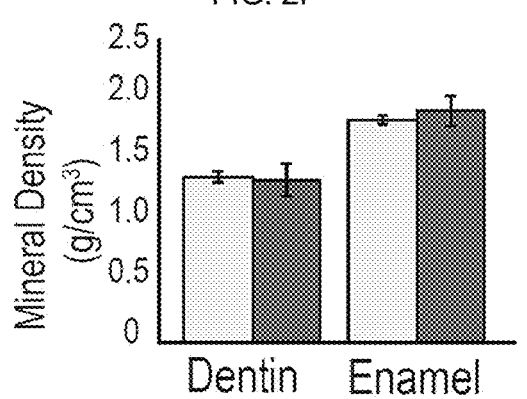
FIG. 2G      FIG. 2H

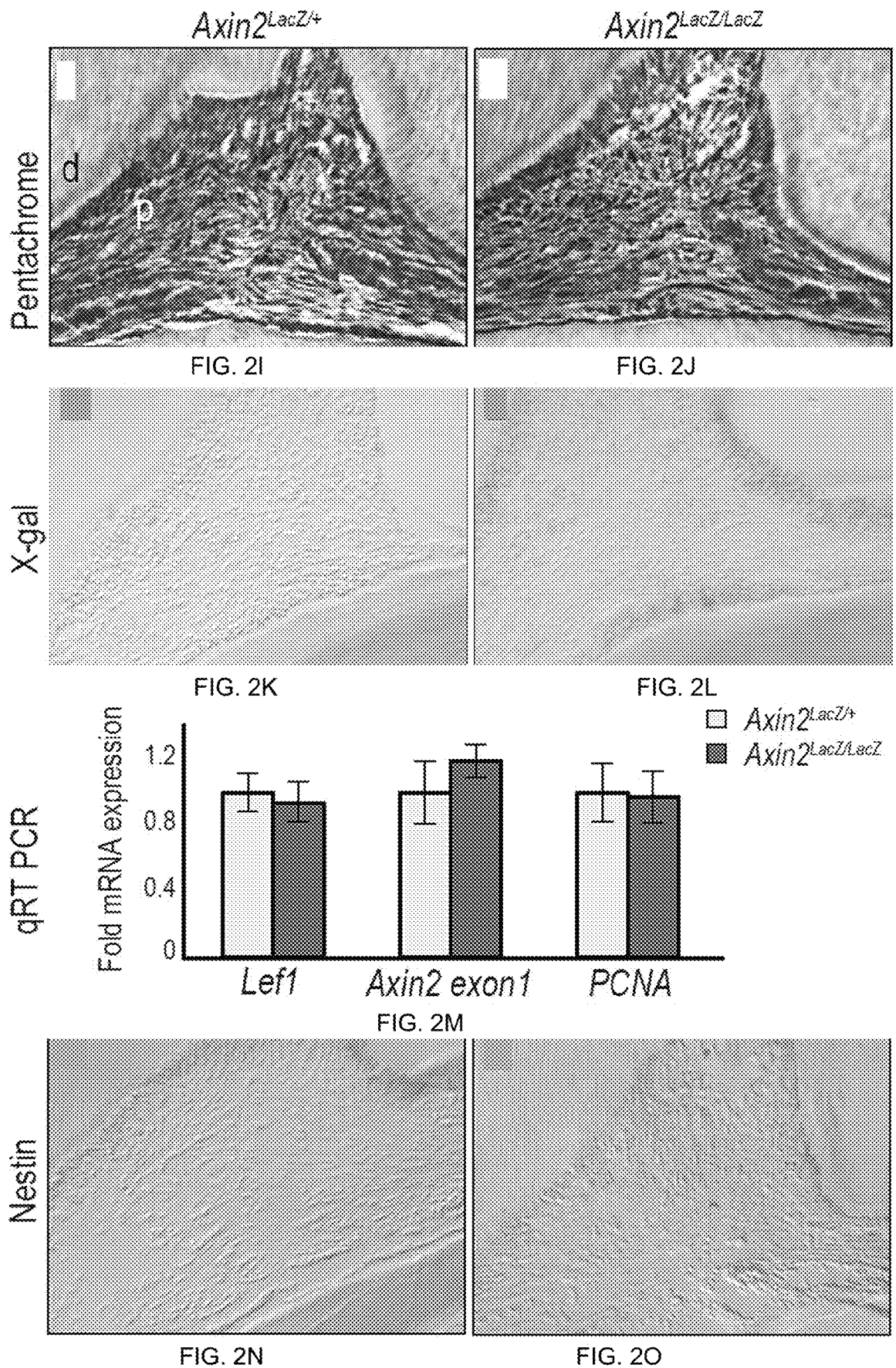

FIG. 3A $Axin2^{LacZ/+}$
FIG. 3B $Axin2^{LacZ/LacZ}$
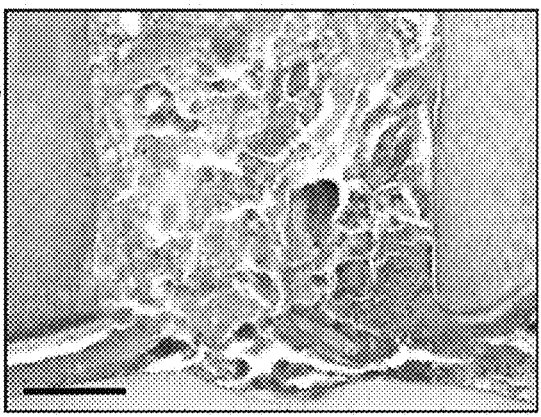
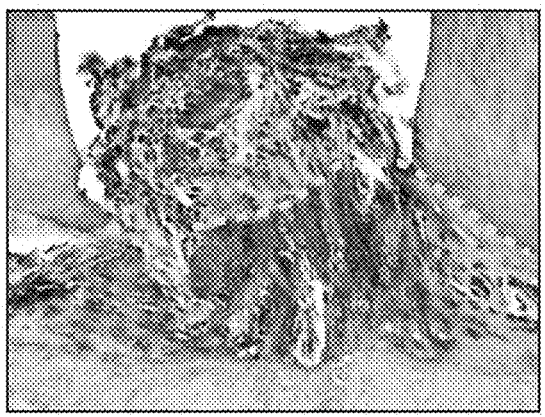
FIG. 3C
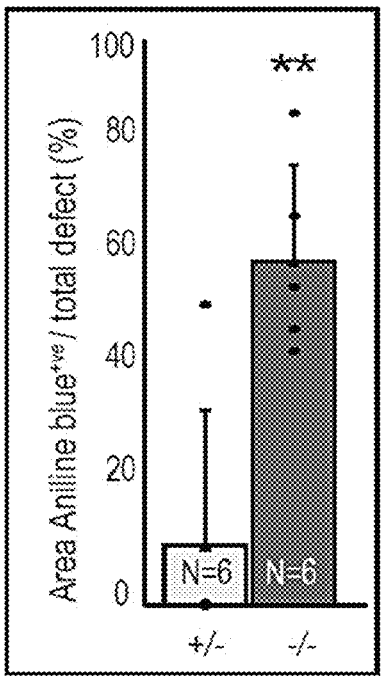
FIG. 3D $Axin2^{LacZ/+}$
FIG. 3E $Axin2^{LacZ/LacZ}$
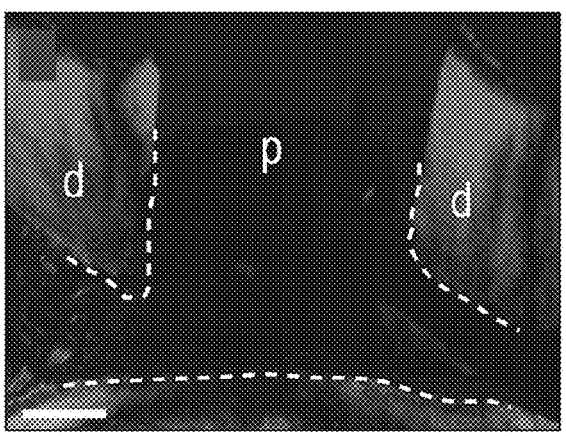
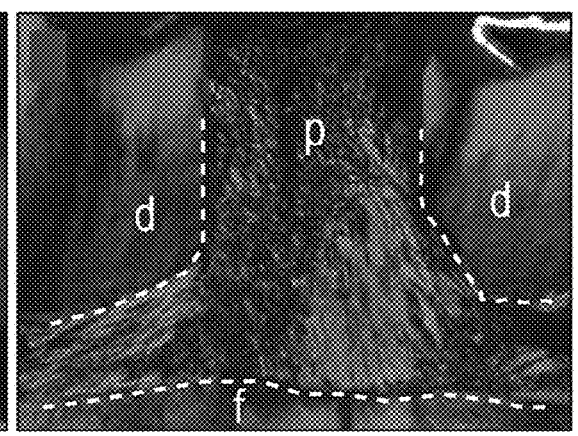

FIG. 3F  *Axin2$^{LacZ/+}$*    FIG. 3G  *Axin2$^{LacZ/LacZ}$*
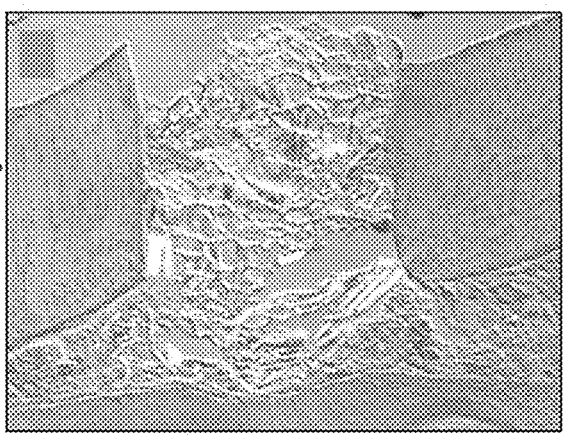 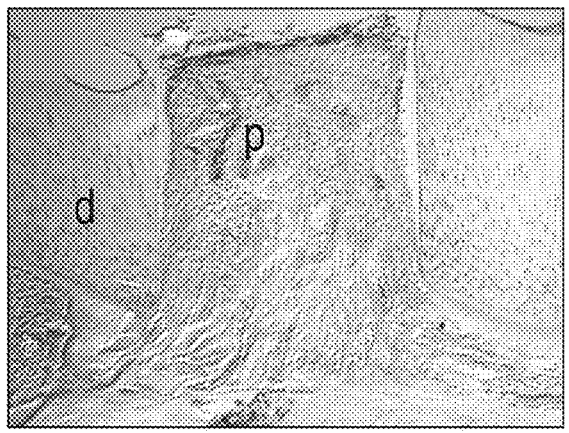
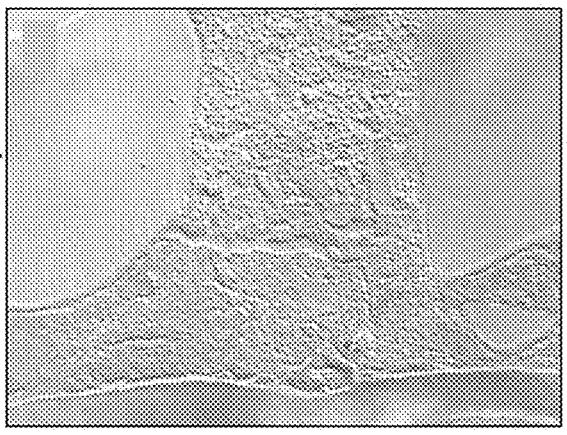 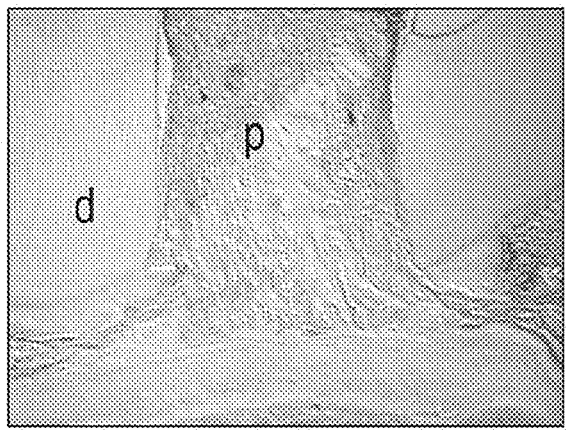
FIG. 3H                    FIG. 3I FIG. 3J  *Axin2^{LacZ/+}*

FIG. 3K  *Axin2^{LacZ/LacZ}*

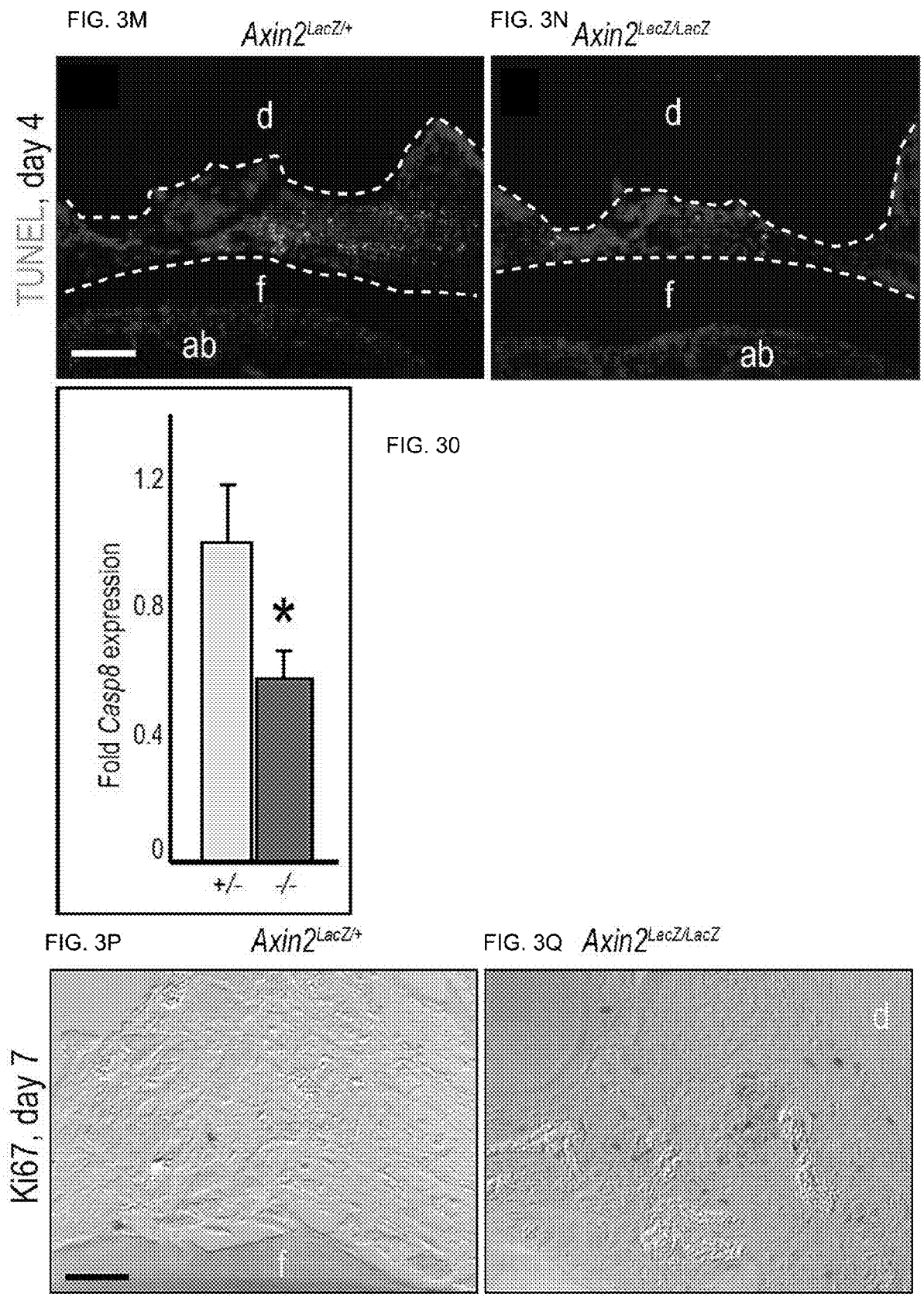

FIG. 5A L-PBS  FIG. 5B L-WNT3A
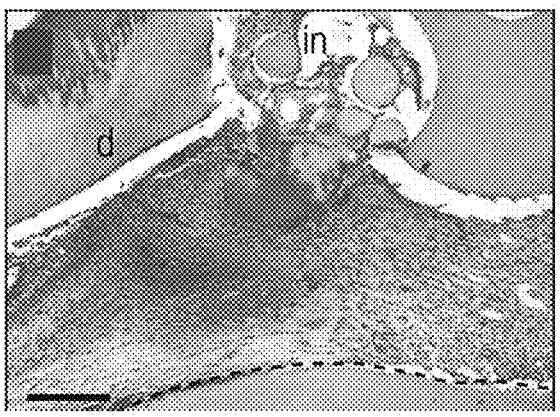
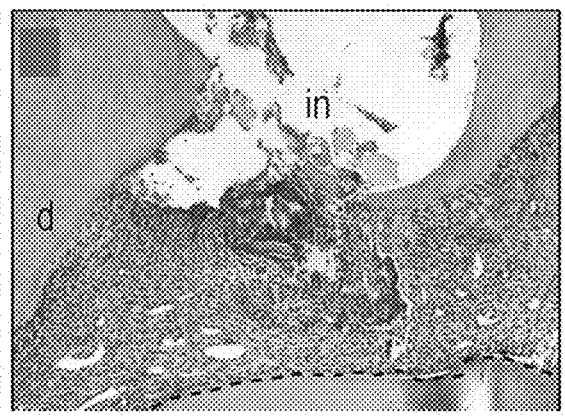
Pentachrome, day 4
FIG. 5C  FIG. 5D
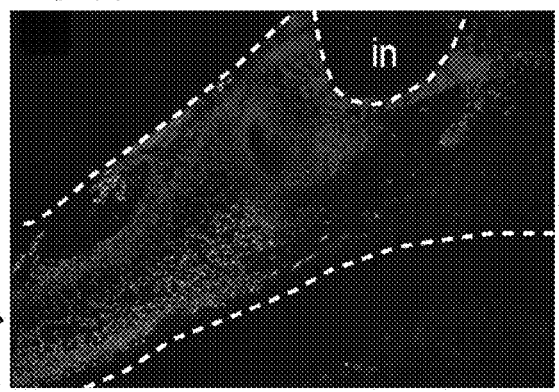
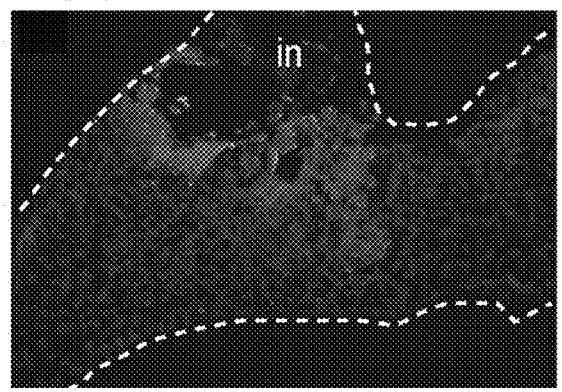
TUNEL, day 4
FIG. 5C(i)  FIG. 5D(i)
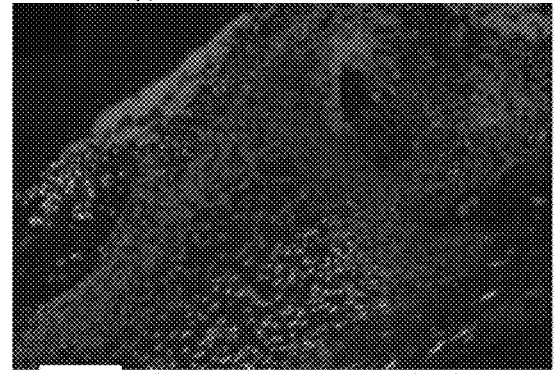
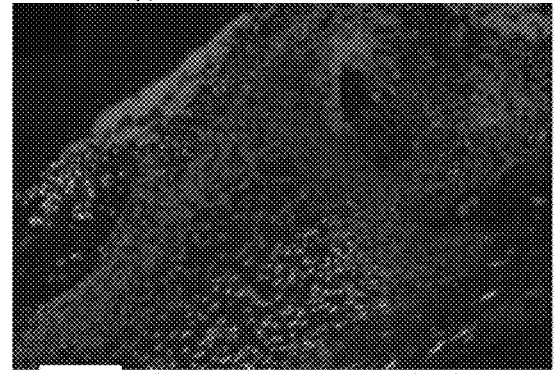
FIG. 5E  FIG. 5F
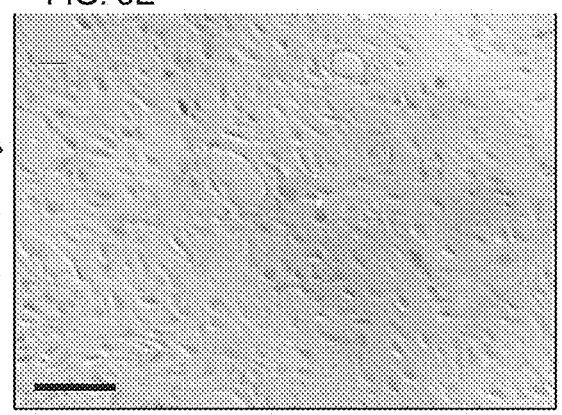
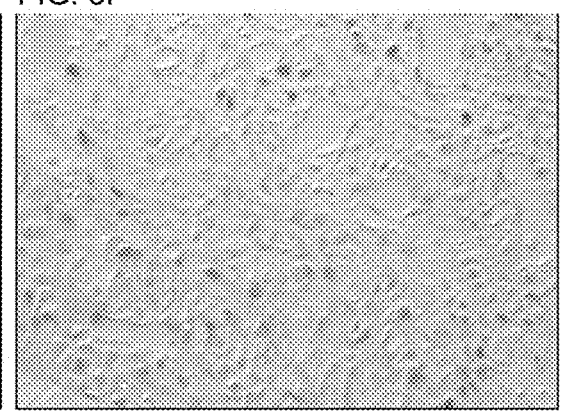
PCNA, day 4

FIG. 5G
L-PBS
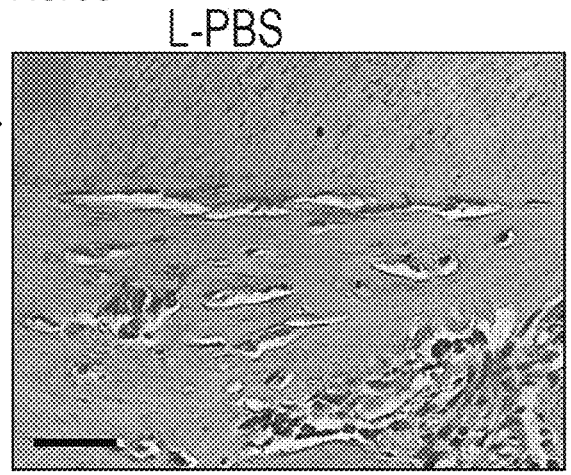
Pentachrome, day 14
FIG. 5H
L-WNT3A
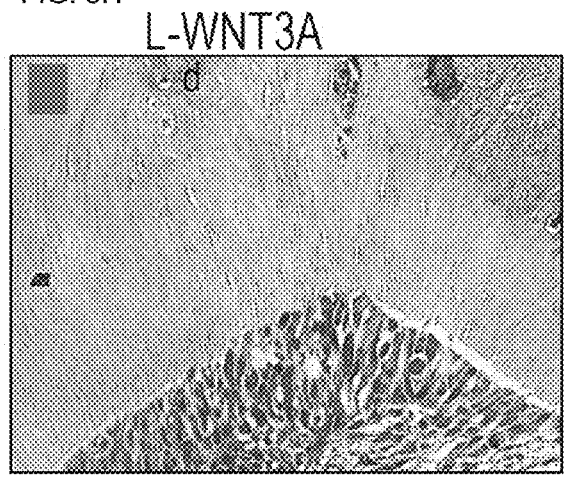
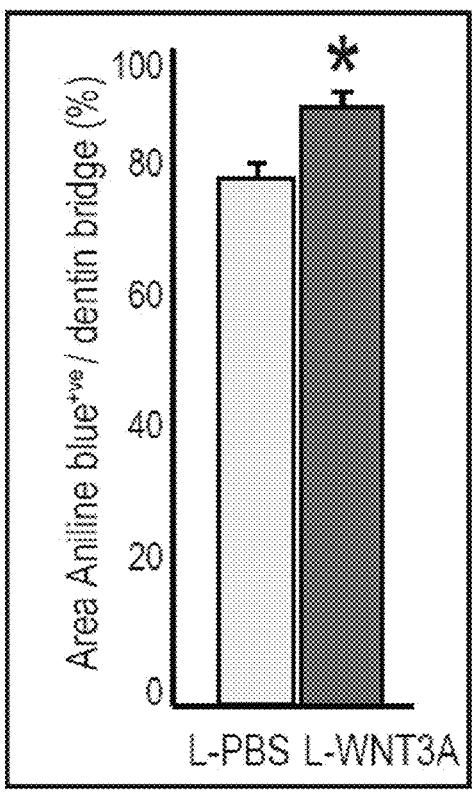
FIG. 5I FIG. 5J  
L-PBS
FIG. 5K  
L-WNT3A
PR/polarized λ, day 14
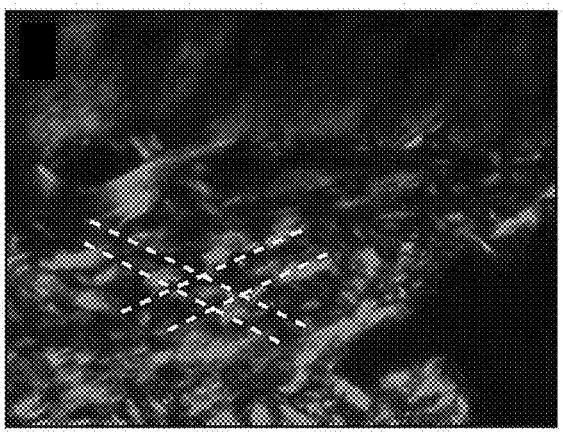
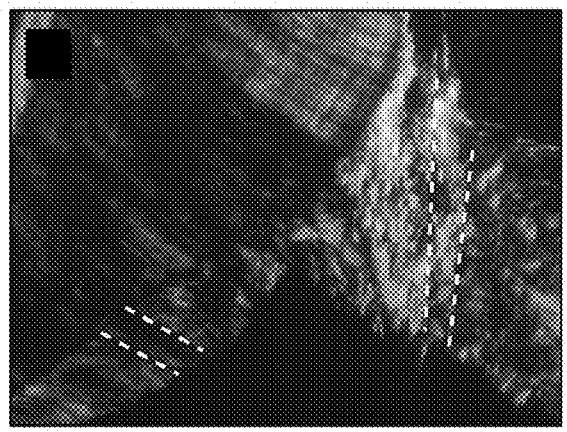
FIG. 5L
FIG. 5M
Nestin, day 14
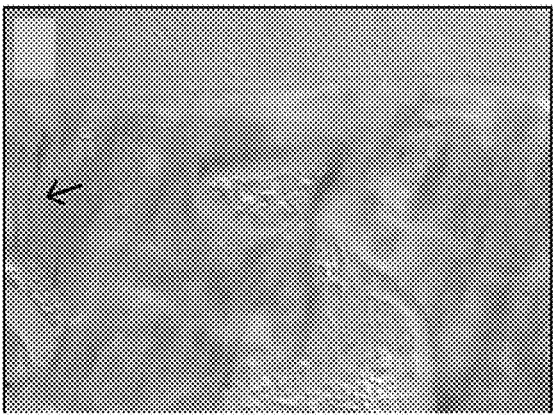
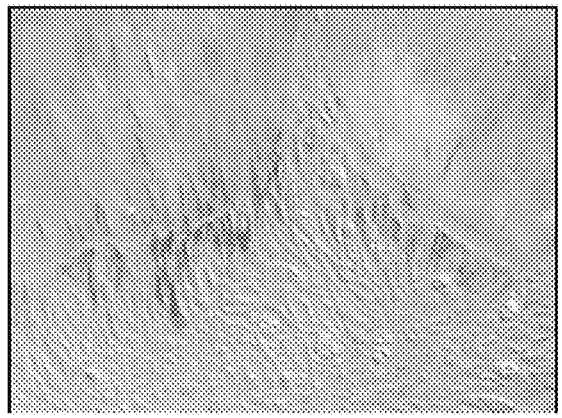
FIG. 5N
FIG. 5O
DSP, day 14
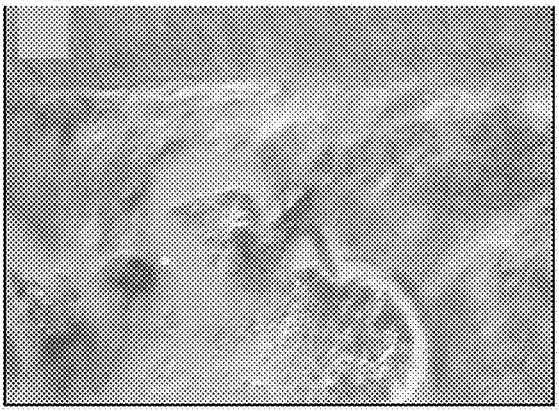

FIG. 6A Pentachrome
FIG. 6B Axin2$^{LacZ/+}$ X-gal
FIG. 6C Lef1
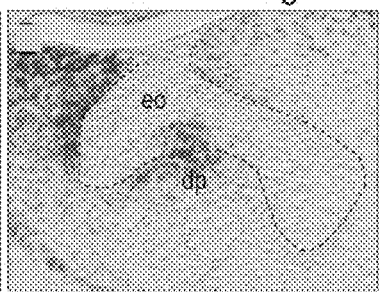
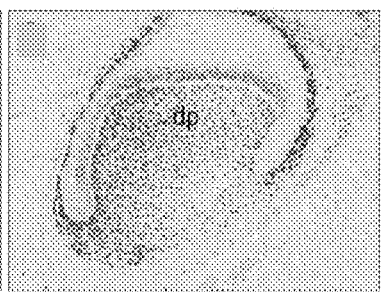
PAS
DSP
Axin2$^{LacZ/+}$ X-gal
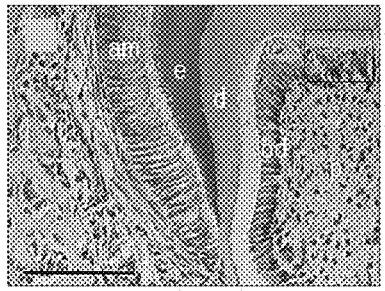
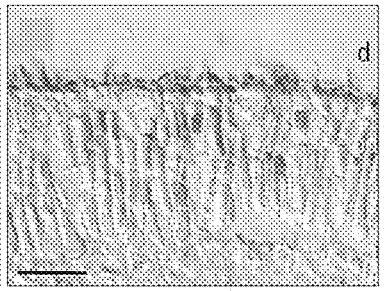
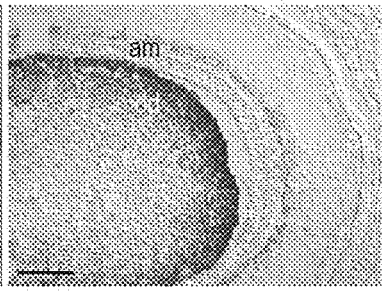
FIG. 6D
FIG. 6E
FIG. 6F

Healthy tooth

Examples of pulp exposure

FIG. 8A Pentachrome
FIG. 8B GFP
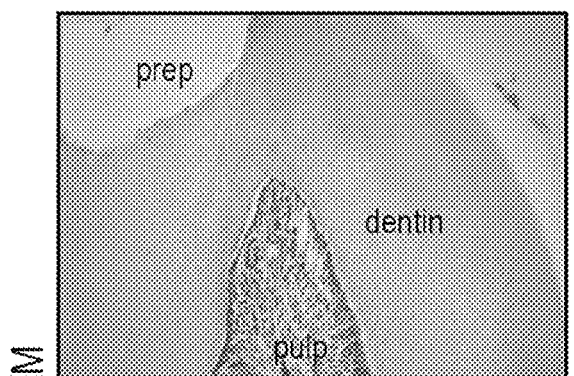
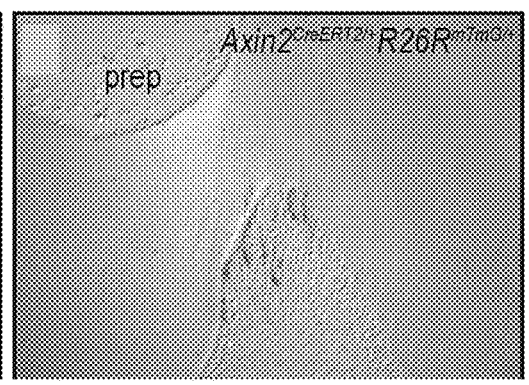
FIG. 8B(i)
FIG. 8B(ii)
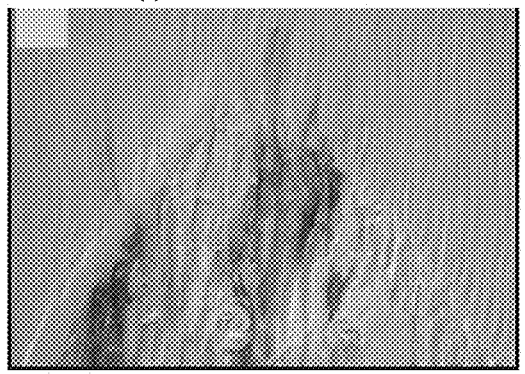
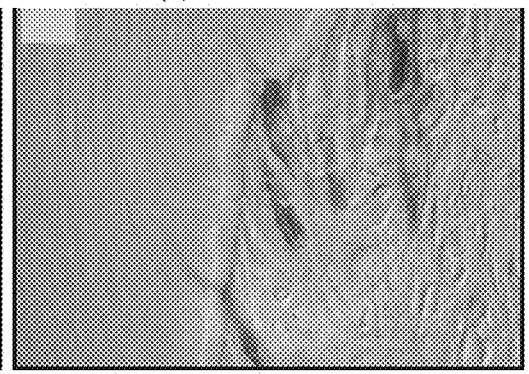
FIG. 8C Pentachrome
FIG. 8D Aniline Blue
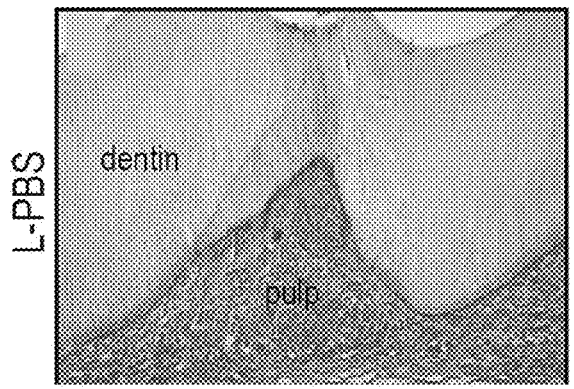
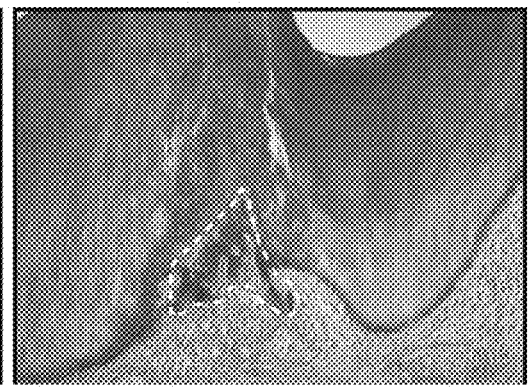
FIG. 8E
FIG. 8F
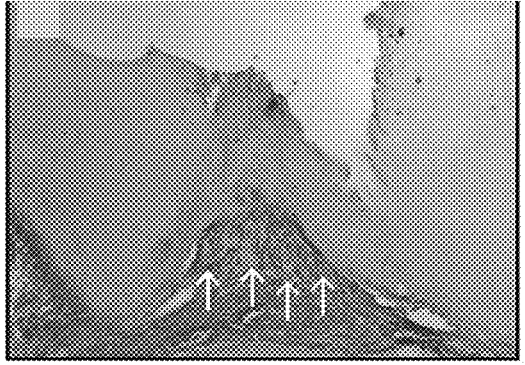
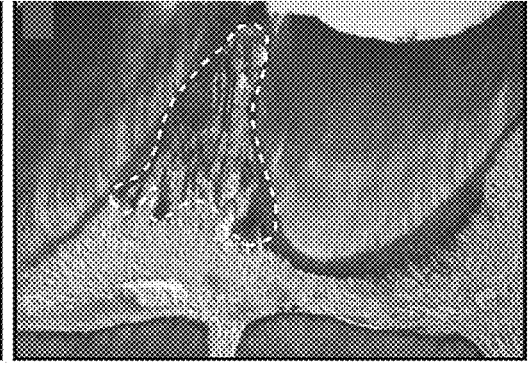

SEQUENCE LISTING

```
<160> NUMBER OF SEQ ID NOS: 19

<210> SEQ ID NO 1
<211> LENGTH: 19
<212> TYPE: DNA
<213> ORGANISM: Artificial sequence
<220> FEATURE:
<223> OTHER INFORMATION: Synthetic nucleotide

<400> SEQUENCE: 1
accctgggcc actttaaag                                                  19

<210> SEQ ID NO 2
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 2
ccttcataca tcgggagcac                                                 20

<210> SEQ ID NO 3
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 3
tcagtaacag cccaagaacc                                                 20

<210> SEQ ID NO 4
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 4
gagcctcctc tctttacagc                                                 20

<210> SEQ ID NO 5
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 5
gcactggaat gtcatctcgc t                                               21
```

<210> SEQ ID NO 6
<211> LENGTH: 22
<212> TYPE: DNA
<213> ORGANISM: Artificial sequence
<220> FEATURE:
<223> OTHER INFORMATION: Synthetic nucleotide

<400> SEQUENCE: 6
ggcccatgaa tgtctctctg ag                                    22

<210> SEQ ID NO 7
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 7
acaccctgat gaaggaaagc                                       20

<210> SEQ ID NO 8
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 8
gacccatttg acatgtacgg                                       20

<210> SEQ ID NO 9
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 9
cttggaatcc cagaacagga                                       20

<210> SEQ ID NO 10
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 10
cagcatctcc aatgtggcta                                       20

<210> SEQ ID NO 11
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 11
ctcgggagag tcgcttagag                                       20

<210> SEQ ID NO 12
<211> LENGTH: 19
<212> TYPE: DNA
<213> ORGANISM: Artificial sequence
<220> FEATURE:

```
<223> OTHER INFORMATION: Synthetic nucleotide

<400> SEQUENCE: 12
cacagccagc tggaacttt                                                19

<210> SEQ ID NO 13
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 13
ggaatggaga gaggactgct                                               20

<210> SEQ ID NO 14
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 14
aggtgttgtc tccgtcagtg                                               20

<210> SEQ ID NO 15
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 15
tgtgacgagc tatcaaacca g                                             21

<210> SEQ ID NO 16
<211> LENGTH: 21
<212> TYPE: DNA
<213> ORGANISM: Artificial sequence
<220> FEATURE:
<223> OTHER INFORMATION: Synthetic nucleotide

<400> SEQUENCE: 16
gaggatcaag ttctggagag c                                             21

<210> SEQ ID NO 17
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 17
aaggacaaga ggcacgtctg                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic nucleotide

<400> SEQUENCE: 18
cgctgttctt gcagtggtag                                               20
```

-continued

```
<210> SEQ ID NO 19
<211> LENGTH: 352
<212> TYPE: PRT
<213> ORGANISM: Homo sapiens

<400> SEQUENCE: 19
```

Met Ala Pro Leu Gly Tyr Phe Leu Leu Leu Cys Ser Leu Lys Gln Ala
1               5                   10                  15

Leu Gly Ser Tyr Pro Ile Trp Trp Ser Leu Ala Val Gly Pro Gln Tyr
            20                  25                  30

Ser Ser Leu Gly Ser Gln Pro Ile Leu Cys Ala Ser Ile Pro Gly Leu
        35                  40                  45

Val Pro Lys Gln Leu Arg Phe Cys Arg Asn Tyr Val Glu Ile Met Pro
50                  55                  60

Ser Val Ala Glu Gly Ile Lys Ile Gly Ile Gln Glu Cys Gln His Gln
65                  70                  75                  80

Phe Arg Gly Arg Arg Trp Asn Cys Thr Thr Val His Asp Ser Leu Ala
                85                  90                  95

Ile Phe Gly Pro Val Leu Asp Lys Ala Thr Arg Glu Ser Ala Phe Val
            100                 105                 110

His Ala Ile Ala Ser Ala Gly Val Ala Phe Ala Val Thr Arg Ser Cys
        115                 120                 125

Ala Glu Gly Thr Ala Ala Ile Cys Gly Cys Ser Ser Arg His Gln Gly
130                 135                 140

Ser Pro Gly Lys Gly Trp Lys Trp Gly Gly Cys Ser Glu Asp Ile Glu
145                 150                 155                 160

Phe Gly Gly Met Val Ser Arg Glu Phe Ala Asp Ala Arg Glu Asn Arg
                165                 170                 175

Pro Asp Ala Arg Ser Ala Met Asn Arg His Asn Asn Glu Ala Gly Arg
            180                 185                 190

Gln Ala Ile Ala Ser His Met His Leu Lys Cys Lys Cys His Gly Leu
        195                 200                 205

Ser Gly Ser Cys Glu Val Lys Thr Cys Trp Trp Ser Gln Pro Asp Phe
210                 215                 220

Arg Ala Ile Gly Asp Phe Leu Lys Asp Lys Tyr Asp Ser Ala Ser Glu
225                 230                 235                 240

Met Val Val Glu Lys His Arg Glu Ser Arg Gly Trp Val Glu Thr Leu
                245                 250                 255

Arg Pro Arg Tyr Thr Tyr Phe Lys Val Pro Thr Glu Arg Asp Leu Val
            260                 265                 270

Tyr Tyr Glu Ala Ser Pro Asn Phe Cys Glu Pro Asn Pro Glu Thr Gly
        275                 280                 285

Ser Phe Gly Thr Arg Asp Arg Thr Cys Asn Val Ser Ser His Gly Ile
290                 295                 300

Asp Gly Cys Asp Leu Leu Cys Cys Gly Arg Gly His Asn Ala Arg Ala
305                 310                 315                 320

Glu Arg Arg Arg Glu Lys Cys Arg Cys Val Phe His Trp Cys Cys Tyr
                325                 330                 335

Val Ser Cys Gln Glu Cys Thr Arg Val Tyr Asp Val His Thr Cys Lys
            340                 345                 350

COMPOSITIONS AND METHODS FOR DELIVERING LYOPHILIC AGENTS TO DENTAL PULP AND FOR ENHANCING DENTIN PRODUCTION

CROSS REFERENCE

This application claims benefit and is a Continuation of 371 application Ser. No. 15/539,489, filed Jun. 23, 2017, which claims benefit of PCT Application No. PCT/US2015/067683, filed Dec. 28, 2015, which claims benefit of U.S. Provisional Patent Application No. 62/097,502, filed Dec. 29, 2014, which applications are incorporated herein by reference in their entirety.

INTRODUCTION

Many toothaches are the result of chronic bacterial infections that cause inflammation of the connective, vascular, lymphatic and nervous tissues occupying a chamber in the center of the tooth. When these tissues, collectively referred to as the pulp, become chronically inflamed they must be removed in a procedure known as a root canal treatment. Even when bacterial infections do not penetrate into the pulp chamber, a root canal may be required because bacterial by-products can diffuse through the remaining tooth structure and cause chronic pulp inflammation. In an effort to treat these conditions, a century's old procedure called pulp capping is often employed, which consists of placing a material such as calcium hydroxide on the remaining tooth structure that creates a high pH, antimicrobial environment.

Tooth sensitivity affects millions of people and can be traced to an inadequate amount of dentin insulating the pulp cavity. Normally, dentin is insulated by enamel on the crown of the tooth, and by gum tissue on the roots of the teeth. Tooth sensitivity can occur when these insulators deteriorate. For example, tooth sensitivity can arise because of a deep cavity, a deep dental restoration (e.g., amalgam, composite, a crown, etc.), periodontal disease, or because of aging.

One goal of regenerative dental medicine is to stimulate the generation of dentin (e.g., from odontoblasts) with the same structural and biological properties of native dentin. In doing so, the vitality and function of the existing teeth can be preserved. Odontoblasts secrete an extracellular matrix that undergoes mineralization and are trapped within the pulp chamber. Unless the pulp cavity has been exposed, delivery of medicants (e.g., therapeutic agents) to pulpal tissues is difficult. The pulp is surrounded by dentin, a mineralized matrix that protects the pulp cavity from thermal, chemical and other noxious stimuli. The only means to access the pulp is either through mechanical exposure (drilling) or delivery of the medicant via the dentinal tubules. Dentinal tubules are small (2.5 µm diameter), fluid filled cannuli that house the odontoblastic process.

The present disclosure provides compositions and methods for delivering lipophilic agents to pulp tissue, and/or for enhancing dentin production by dental pulp tissue (e.g., in the context of pulp exposure, tooth sensitivity, and the like).

PUBLICATIONS

Han et al., PLoS One. 2014 Feb. 10; 9(2):e88890; Yang and Liu, Stem Cells In Oral Medicine. 2012; 1(1): 3-8; Arioka et al., Biochem Pharmacol. 2014 Aug. 15; 90(4): 397-405; Biomaterials. 2015 January; 39:145-54, Epub 2014 Nov. 22; Thesleff and Tummers, StemBook [Internet]. Cambridge (Mass.): Harvard Stem Cell Institute; 2008-2009 Jan. 31; Minear et al., Sci Transl Med. 2010 Apr. 28; 2(29):29ra30; Westendorf et al., Gene. 2004 Oct. 27; 341: 19-39; Moon et. al., Nat Rev Genet. 2004 September; 5(9):691-701; Dhamdhere et al., PLoS One. 2014 Jan. 6; 9(1):e83650; Zhao et al., Methods Enzymol. 2009; 465:331-47; U.S. patent publication numbers: 20140371151, 20120115788, 20120329790, 20120231091, and 20080226707; PCT publication number WO2012122081; and U.S. Pat. No. 8,809,272.

SUMMARY

Methods and compositions are provided for enhancing dentin production, and for delivering a lipophilic agent to pulp tissue of a tooth of an individual. In some embodiments, a subject method includes a step of administering to the pulp of a tooth of an individual, a Wnt stimulating composition that includes a Wnt stimulator agent, at a dose sufficient to enhance the production of dentin by the pulp. In some cases, the pulp is exposed pulp and the administering step includes contacting the exposed pulp with the Wnt stimulating composition. In some cases, the administering step includes a step of contacting dentin with the Wnt stimulating composition, whereby the Wnt stimulating composition penetrates the dentin to the underlying pulp tissue. In some cases, the Wnt stimulating composition includes a lipophilic Wnt stimulator agent inserted in the non-aqueous phase of a lipid structure. In some such cases, the lipophilic Wnt stimulator agent is a Wnt protein (e.g., a Wnt protein having a lipid moiety). In some cases, the Wnt protein is Wnt3A (e.g., human Wnt3A). Thus, in some cases, the Wnt stimulating composition includes a liposomal Wnt (L-Wnt), e.g., liposomal Wnt3A (L-Wnt3A).

In some embodiments, a subject method includes a step of contacting exposed dentin of a tooth with a composition that includes a lipophilic agent inserted in the non-aqueous phase of a lipid structure (e.g., whereby the lipophilic agent penetrates the dentin to the underlying pulp tissue). In some cases, the individual has tooth sensitivity or is at risk of developing tooth sensitivity (e.g., following a dental procedure). In some cases, the pulp of the tooth is exposed and in some cases, the pulp of the tooth is not exposed. In some cases, a subject method includes, prior to the contacting step, a step of exposing dentin of the tooth. In some cases, the lipophilic agent is a growth factor having a lipid moiety. In some cases, the lipophilic agent is a Wnt stimulator agent having a lipid moiety. In some such cases, the Wnt stimulator agent is a Wnt protein (e.g., a Wnt protein having a lipid moiety). In some cases, the Wnt protein is Wnt3A (e.g., human Wnt3A). Thus, in some cases, the lipophilic agent inserted in the non-aqueous phase of a lipid structure is a liposomal Wnt (L-Wnt), e.g., liposomal Wnt3A (L-Wnt3A).

In some cases, a Wnt3A protein is delivered to the pulp cavity. The lipophilic WNT3A protein can be tethered to a lipid vesicle, which can stabilize the in vivo biological activity of the protein. The liposomal Wnt3A (L-Wnt3A) formulation can be applied to exposed dentin, whereby the liposomal particles penetrate the dentin through the dentinal tubules, which extend from the outside of the tooth to the pulp cavity. There, L-Wnt3A can enhance both the survival and proliferation of pulp cells, and can stimulate the formation of dentin (e.g., tertiary dentin), which insulates the tooth and protects the pulp from thermal and chemical insult. By stimulating new dentin formation, the risk of bacterial infection of the pulp and overall tooth sensitivity are reduced and the need for root canal therapies, extensive prosthetic replacements, and tooth extraction are reduced. The subject methods can augment the body's natural response to tooth sensitivity: topical application of a liposomal protein therapeutic can stimulate dental pulp cells to produce more dentin and in doing so, provide additional insulation to the teeth. The subject methods have broad applications in general restorative dentistry, prosthodontics, and periodontics. Kits are provided for practicing the methods of the disclosure.

BRIEF DESCRIPTION OF THE DRAWINGS

The invention is best understood from the following detailed description when read in conjunction with the accompanying drawings. The patent or application file contains at least one drawing executed in color. Copies of this patent or patent application publication with color drawing(s) will be provided by the Office upon request and payment of the necessary fee. It is emphasized that, according to common practice, the various features of the drawings are not to-scale. On the contrary, the dimensions of the various features are arbitrarily expanded or reduced for clarity. Included in the drawings are the following figures.

FIG. 1B Higher magnification of the pulpal-dentin complex illustrates the organization of pulp cells and odontoblasts (pink) juxtaposed to the pre-dentin and dentin (blue and blue-yellow). FIG. 1C In the pulp cavity only polarized, secretory odontoblasts are positive for Nestin immunostaining. FIG. 1D These polarized, secretory odontoblasts express DSP. FIG. 1E X-gal staining and FIG. 1F GFP fluorescence, respectively in adult $Axin2^{LacZ/+}$ and $Axin2^{CreERT2/+}$; $R26R^{mTmG/+}$ mice, demonstrates that polarized, secretory odontoblasts and pulp cells are Wnt responsive. Abbreviations: ab, alveolar bone; d, dentin; od, odontoblast; p, pulp; pd, pre-dentin. Scale bars: 400 µm FIG. 1A, 25 µm FIG. 1B-1E, 10 µm FIG. 1F.

FIG. 2A-2P. Axin2 deletion does not disrupt odontogenesis or pulpal-dentin homeostasis. (FIG. 2A-2F) Microcomputed tomography (µCT) reconstructions of the molar region in skeletally mature, male (FIGS. 2A, 2C, 2E) $Axin2^{LacZ/+}$ and (FIG. 2B, 2D, 2F) $Axin2^{LacZ/LacZ}$ mice. Quantified µCT demonstrate no differences in (FIG. 2G) dentin volume, or (FIG. 2H) dentin and enamel mineral density in molars from age-matched, sex-matched, adult $Axin2^{LacZ/+}$ and $Axin2^{LacZ/LacZ}$ mice. Pentachrome staining indicates the cellularity and organization of the pulp cavities from (FIG. 2I) $Axin2^{LacZ/+}$ and (FIG. 2J) $Axin2^{LacZ/LacZ}$ mice. (FIG. 2K) X-gal staining in odontoblasts and sub-odontoblasts in $Axin2^{LacZ/+}$ and (L) $Axin2^{LacZ/LacZ}$ mice; the stronger staining in (FIG. 2L) is due to $Axin2^{LacZ/LacZ}$ mice carrying two copies of the LacZgene. (FIG. 2M) Quantitative RT-PCR analyses of pulp tissues from $Axin2^{LacZ/+}$ and $Axin2^{LacZ/LacZ}$ mice, evaluated for the relative expression levels of Left, Axin2 exon1, and PCNA. (FIG. 2N) Nestin immunostaining in $Axin2^{LacZ/+}$ and (FIG. 2P) $Axin2^{LacZ/LacZ}$ mice. (FIG. 2P) Quantitative qRT-PCR analyses of pulp tissues from $Axin2^{LacZ/+}$ and $Axin2^{LacZ/LacZ}$ mice, evaluated for expression of Nestin, DSPP, OC, and Col1. Abbreviations: ab, alveolar bone; d, dentin; p, pulp. Scale bars: 500 µm (FIG. 2A-2F), and 100 µm (FIG. 2I-2L and FIG. 2N-2O).

(FIG. 3A) In $Axin2^{LacZ/+}$ mice on day 14, pentachrome staining identifies a pink-colored, acellular granulation tissue that occupies the pulp injury site.

FIG. 4A Quantitative RT-PCR analyses following 6, 12, 24 hours of L-PBS or L-WNT3A treatment of human dental pulp stem cells. FIG. 4B Twelve hours post treatment, the proliferative capacity of hDPSCs was assayed using the BrdU incorporation. FIG. 4C Quantitative RT-PCR for CASP3 expression. FIG. 4D Quantitative RT-PCR analyses following 6, 12, 24 hours of L-PBS or L-WNT3A treatment of whole bone marrow cells. FIG. 4E Twelve hours after whole bone marrow cells were exposed to L-WNT3A and L-PBS Ki67 expression and FIG. 4F TUNEL activity were evaluated. Scale bars: 100 µm (FIG. 4B, 4E, 4F). Single asterisk denotes P<0.05. Error Bars represent SEM.

FIG. 5A-5O. L-WNT3A treatment induces dentin regeneration. Pentachrome staining of pulp injuries on post-injury day 4 in FIG. 5A L-PBS treated rats and in FIG. 5B L-WNT3A treated rats. Post-surgical day 4, TUNEL staining in the pulp cavities of FIG. 5C, 5C(i) L-PBS and FIG. 5D, 5D(i) L-WNT3A treated rats. On post-surgical day 4, PCNA expression in the pulp cavities of FIG. 5E L-PBS and FIG. 5F L-WNT3A treated rats. Pentachrome staining of FIG. 5G L-PBS and FIG. 5H L-WNT3A treated rats 14 days after injury. FIG. 5I Quantification of reparative dentin matrix. Under polarized light, Picrosirius red staining of pulp injuries on post-injury day 14 in FIG. 5J L-PBS and FIG. 5K L-WNT3A treated injury sites. On post-surgical day 14, Nestin expression in FIG. 5L L-PBS and FIG. 5M L-WNT3A treated rats, and DSP expression in FIG. 5N L-PBS and FIG. 5O L-WNT3A treated rats. Abbreviations: dentin, d; in, injury site. Scale bars: 200 µm FIG. 5A-5D, 100 µm FIG. 5C(i), 5D(i), 50 µm FIG. 5E-5F, 25 µm FIG. 5G-5O, 50 µm. Single asterisk denotes P<0.01. Error Bars represent SEM.

FIG. 6A-6F. In an embryonic 18.5 mouse molar FIG. 6A pentachrome staining identifies the enamel organ (dotted lines) and dental mesenchyme. FIG. 6B X-gal staining of a molar tooth bud from an $Axin2^{LacZ/+}$ embryo. On an adjacent tissue section, FIG. 6C Lef1 immunostaining identifies Wnt responsive cells in the outer enamel organ and in the condensing dental mesenchyme. At post-natal day 7, FIG. 6D periodic acid schiff staining identifies polarized odontoblasts and their newly secreted dentin matrix (pink), which approximates newly secreted enamel matrix (red) produced by ameloblasts. FIG. 6E These polarized, secretory odontoblasts express DSP. FIG. 6F In Axin2$^{LacZ/+}$ mice, X-gal staining demonstrates that polarized, secretory odontoblasts are Wnt responsive. Abbreviations: am, ameloblasts; ab, alveolar bone; d, dentin; df, dental follicle; dp, dental papilla; e, enamel; eo, enamel organ; m, dental mesenchyme; od, odontoblast; p, pulp; pd, pre-dentin. Scale bars: 100 μm FIG. 6A-6C, 100 μm FIG. 6D, 25 μm FIG. 6E-6F.

FIG. 8A-8F. FIG. 8A A non-penetrating cavity preparation, simulating that seen in humans, that cuts through the tubular dentin (yellow) but does not penetrate to the pulp cavity (pink). FIG. 8B An adjacent section to FIG. 8A, stained to identify cells expressing GFP. These cavity preparations were generated in transgenic mice that, in the presence of tamoxifen, undergo a recombination event where Wnt responsive cells express GFP. Pulp cells are Wnt responsive, and in this animal, tamoxifen was delivered via liposomal particles identical to those used to delivery WNT3A protein. The GFP positive cells therefore represent Wnt responsive cells in the pulp cavity whose only means of tamoxifen exposure was via the dentinal tubules. FIG. 8B(i) and FIG. 8B(ii) show higher magnification of the Wnt-responsive odontoblasts that express GFP as a consequence of liposomal tamoxifen delivery. FIG. 8C-8D The pulp response to the cavity preparation (that cuts through the tubular dentin but does not penetrate to the pulp cavity) and topical liposomal PBS delivery. A small amount of reparative dentin is generated (dotted white line in FIG. 8D), in keeping with the body's natural ability to stimulate a repair response. FIG. 8E-8F The pulp response to a similar cavity preparation as in panels FIG. 8C-8D, and topical L-WNT3A delivery to exposed dentin. Significantly more reparative dentin is observed in the pulp chamber.

DETAILED DESCRIPTION

Figure 1A:
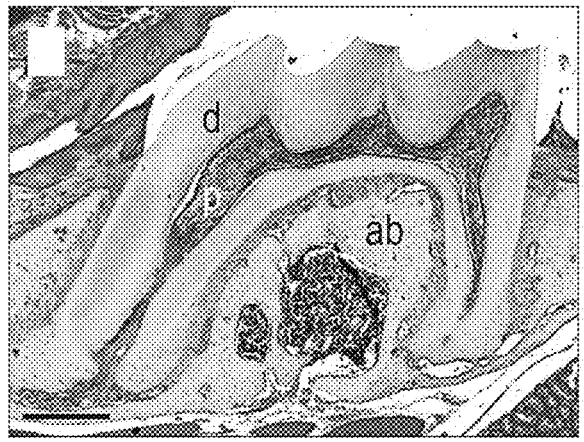
FIG. 1A-1F. Odontoblasts are Wnt responsive FIG. 1A In skeletally mature mice, pentachrome staining identifies dentin (yellow to yellow-green), pulp (purple) and alveolar bone (yellow).
Figure 1B:
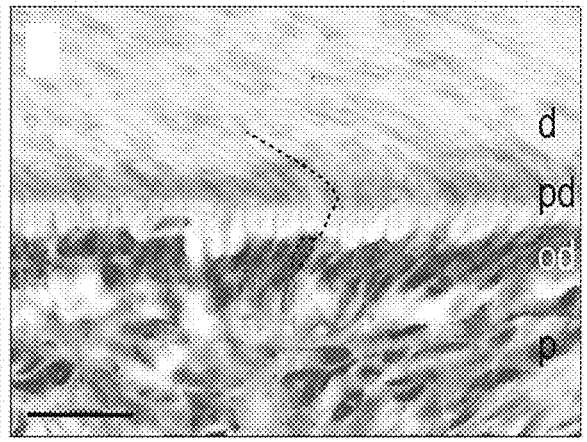

Methods and compositions are provided for enhancing dentin production, and for delivering a lipophilic agent to pulp tissue of a tooth of an individual. In some cases, a subject method includes a step of administering to the pulp of a tooth of an individual, a Wnt stimulating composition that includes a Wnt stimulator agent, at a dose sufficient to enhance the production of dentin by the pulp. In some cases, a subject method includes a step of contacting exposed dentin of a tooth with a composition that includes a lipophilic agent inserted in the non-aqueous phase of a lipid structure (e.g., whereby the lipophilic agent penetrates the dentin to the underlying pulp tissue). Kits are also provided for practicing the methods of the disclosure.

Before the present methods and compositions are described, it is to be understood that this invention is not limited to particular method or composition described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

It must be noted that as used herein and in the appended claims, the singular forms "a", "an", and "the" include plural referents unless the context clearly dictates otherwise. Thus, for example, reference to "a cell" includes a plurality of such cells and reference to "the peptide" includes reference to one or more peptides and equivalents thereof, e.g. polypeptides, known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Definitions

In the description that follows, a number of terms conventionally used in the field are utilized. In order to provide a clear and consistent understanding of the specification and claims, and the scope to be given to such terms, the following definitions are provided.

The terms "polypeptide," "peptide" and "protein" are used interchangeably herein to refer to a polymer of amino acid residues. The terms also apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, gamma-carboxyglutamate, and O-phosphoserine. Amino acid analogs refers to compounds that have the same basic chemical structure as a naturally occurring amino acid, i.e., an .alpha. carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

The terms "recipient", "individual", "subject", "host", and "patient", are used interchangeably herein and refer to any individual for whom diagnosis, treatment, or therapy is desired, particularly humans. "Mammal" or "mammalian" for purposes of treatment refers to any animal classified as a mammal, including humans, domestic and farm animals, and zoo, sports, or pet animals, such as dogs, horses, cats, cows, sheep, goats, pigs, etc. In some embodiments, the mammal is human.

Compositions

The present disclosure provides compositions and methods for enhancing dentin production by dental pulp tissue. Such methods include administering to the pulp of a tooth of an individual, a Wnt stimulating composition comprising a Wnt stimulator agent, at a dose sufficient to enhance the production of dentin by the pulp. In some cases the Wnt stimulator agent comprises a lipophilic Wnt stimulator agent (e.g., a Wnt protein, such as Wnt3A) inserted in the non-aqueous phase of a lipid structure.

The present disclosure also provides compositions and methods for delivering a lipophilic agent to pulp tissue of a tooth of an individual. In some cases the lipophilic agent is a growth factor (e.g., a growth factor having a lipid moiety). In some cases, the lipophilic agent is a lipophilic Wnt stimulator agent (e.g., a Wnt protein, such as Wnt3A) inserted in the non-aqueous phase of a lipid structure.

Lipid Structure.

In some embodiments, the subject agent (e.g., an agent of interest) is a lipophilic agent inserted in the non-aqueous phase of a lipid structure. Lipid structures can be important for maintaining the activity of lipophilic agents (e.g., Wnt proteins, growth factors, etc., e.g., having a lipid moiety), following in vivo administration. The subject lipophilic agents (e.g., Wnt proteins, growth factors, etc., e.g., having a lipid moiety) are not encapsulated in the aqueous phase of the lipid structures, but are rather integrated into the lipid membrane, and may be inserted in the outer layer of a membrane. Such a structure is not predicted from conventional methods of formulating agents (e.g., proteins) in, for example, liposomes. A Wnt protein integrated within such lipid structure is referred herein as L-Wnt (e.g., Wnt3A integrated into such a lipid structure can be referred to as L-Wnt3A). The methods used for tethering lipophilic agents (e.g., Wnt proteins) to the external surface of a liposome or micelle can utilize a moiety (e.g., a protein might have an amino acid sequence) so as to emphasize the exoliposomal display of the protein. In some cases, crude liposomes are first pre-formed and a lipophilic agent (e.g., a Wnt protein, a growth factors, etc., e.g., having a lipid moiety) can then be added to the crude mixture, which will favor addition of exo-liposomal agent (e.g., Wnt protein), followed by various formulation steps, which may include size filtering; dialysis, and the like. Suitable lipids include fatty acids, neutral fats such as triacylglycerols, fatty acid esters and soaps, long chain (fatty) alcohols and waxes, sphingoids and other long chain bases, glycolipids, sphingolipids, carotenes, polyprenols, sterols, and the like, as well as terpenes and isoprenoids. For example, molecules such as diacetylene phospholipids may find use. Included are cationic molecules, including lipids, synthetic lipids and lipid analogs, having hydrophobic and hydrophilic moieties, a net positive charge, and which by itself can form spontaneously into bilayer vesicles or micelles in water. Liposomes manufactured with a neutral charge, e.g. DMPC, can be used. Any amphipathic molecules that can be stably incorporated into lipid micelle or bilayers in combination with phospholipids can be used, with its hydrophobic moiety in contact with the interior, hydrophobic region of the micelle or bilayer membrane, and its polar head group moiety oriented toward the exterior, polar surface of the membrane.

The term "cationic amphipathic molecules" is intended to encompass molecules that are positively charged at physiological pH, and more particularly, constitutively positively charged molecules, comprising, for example, a quaternary ammonium salt moiety. Cationic amphipathic molecules typically consist of a hydrophilic polar head group and lipophilic aliphatic chains. Similarly, cholesterol derivatives having a cationic polar head group may also be useful. See, for example, Farhood et al. (1992) Biochim. Biophys. Acta 1111:239-246; Vigneron et al. (1996) Proc. Natl. Acad. Sci. (USA) 93:9682-9686. Cationic amphipathic molecules of interest include, for example, imidazolinium derivatives (WO 95/14380), guanidine derivatives (WO 95/14381), phosphatidyl choline derivatives (WO 95/35301), and piperazine derivatives (WO 95/14651). Examples of cationic lipids that may be used in the present invention include DOTIM (also called BODAI) (Saladin et al., (1995) Biochem. 34: 13537-13544), DDAB (Rose et al., (1991) BioTechniques 10(4):520-525), DOTMA (U.S. Pat. No. 5,550,289), DOTAP (Eibl and Wooley (1979) Biophys. Chern. 10:261-271), DMRIE (Feigner et al., (1994) J. Bioi. Chern. 269(4): 2550-2561), EDMPC (commercially available from Avanti Polar Lipids, Alabaster, Ala.), DCC hoi (Gau and Huang (1991) Biochem. Biophys. Res. Comm. 179:280-285), DOGS (Behr et al., (1989) Proc. Nat!. Acad. Sci. USA, 86:6982-6986), MBOP (also called MeBOP) (WO 95/14651), and those described in WO 97/00241. While not required for activity, in some embodiments a lipid structure may include a targeting group, e.g. a targeting moiety covalently or non-covalently bound to the hydrophilic head group. Head groups useful to bind to targeting moieties include, for example, biotin, amines, cyano, carboxylic acids, isothiocyanates, thiols, disulfides, ahalocarbonyl compounds, a,p-unsaturated carbonyl compounds, alkyl hydrazines, etc. Chemical groups that find use in linking a targeting moiety to an amphipathic molecule also include carbamate; amide (amine plus carboxylic acid); ester (alcohol plus carboxylic acid), thioether (haloalkane plus sulfhydryl; maleimide plus sulfhydryl), Schiffs base (amine plus aldehyde), urea (amine plus isocyanate), thiourea (amine plus isothiocyanate), sulfonamide (amine plus sulfonyl chloride), disulfide; hyrodrazone, lipids, and the like, as known in the art. For example, targeting molecules may be formed by converting a commercially available lipid, such as DAGPE, a PEG-PDA amine, DOTAP, etc. into an isocyanate, followed by treatment with triethylene glycol diamine spacer to produce the amine terminated thiocarbamate lipid which by treatment with the para-isothiocyanophenyl glycoside of the targeting moiety produces the desired targeting glycolipids. This synthesis provides a water soluble flexible linker molecule spaced between the amphipathic molecule that is integrated into the nanoparticle, and the ligand that binds to cell surface receptors, allowing the ligand to be readily accessible to the protein receptors on the cell surfaces. Further information about liposomal Wnt compositions and their use is found in; U.S. patent publication numbers: 20140371151, 20120115788, and 20080226707; and U.S. Pat. No. 8,809,272; all of which are hereby incorporated by reference in their entirety.

In some cases, liposomes or micelles are used as a delivery vehicle. A liposome is a spherical vesicle with a membrane composed of a phospholipid bilayer. Liposomes can be composed of naturally-derived phospholipids with mixed lipid chains (like egg phosphatidylethanolamine), or of pure surfactant components like DOPE (dioleolylphosphatidylethanolamine). Liposomes often contain a core of encapsulated aqueous solution; while lipid spheres that contain no aqueous material are referred to as micelles. As wnt proteins are present in the lipid phase and not the encapsulated aqueous phase, micelles may be used interchangeably with liposome for the compositions of the present disclosure. The lipids may be any useful combination of known liposome or micelle forming lipids, including cationic lipids, such as phosphatidylcholine, or neutral lipids, such as cholesterol, phosphatidyl serine, phosphatidyl glycerol, and the like.

In some embodiments, the vesicle-forming lipid is selected to achieve a specified degree of fluidity or rigidity, to control the stability of the structure in serum, etc. Liposomes having a more rigid lipid bilayer, or a liquid crystalline bilayer, are achieved by incorporation of a relatively rigid lipid, e.g., a lipid having a relatively high phase transition temperature, e.g., up to 60° C. Rigid, i.e., saturated, lipids contribute to greater membrane rigidity in the lipid bilayer. Other lipid components, such as cholesterol, are also known to contribute to membrane rigidity in lipid bilayer structures. Lipid fluidity is achieved by incorporation of a relatively fluid lipid, typically one having a lipid phase with a relatively low liquid to liquid-crystalline phase transition temperature, e.g., at or below room temperature.

The liposomes may be prepared by a variety of techniques, such as those detailed in Szoka, F., Jr., et al., Ann. Rev. Biophys. Bioeng. 9:467 (1980). Typically, the liposomes are multilamellar vesicles (MLVs), which can be formed by simple lipid-film hydration techniques. In this procedure, a mixture of liposome-forming lipids of the type detailed above dissolved in a suitable organic solvent is evaporated in a vessel to form a thin film, which is then covered by an aqueous medium. The lipid film hydrates to form MLVs, e.g., in some cases with sizes in a range of from 0.1 to 10 microns.

The liposomes, micelles, etc. of the disclosure may have substantially homogeneous sizes in a selected size range, for example, between 0.005 to 0.5 microns (e.g., 0.01 to 0.5 0.02 to 0.5, 0.025 to 0.5, 0.05 to 0.5, 0.075 to 0.5, 0.1 to 0.5, 0.005 to 0.4, 0.01 to 0.4 0.02 to 0.4, 0.025 to 0.4, 0.05 to 0.4, 0.075 to 0.4, 0.1 to 0.4, 0.005 to 0.3, 0.01 to 0.3 0.02 to 0.3, 0.025 to 0.3, 0.05 to 0.3, 0.075 to 0.3, 0.1 to 0.3, 0.005 to 0.2, 0.01 to 0.2 0.02 to 0.2, 0.025 to 0.2, 0.05 to 0.2, 0.075 to 0.2, 0.1 to 0.2, 0.005 to 0.1, 0.01 to 0.1 0.02 to 0.1, 0.025 to 0.1, 0.05 to 0.1, 0.075 to 0.1, 0.02 to 0.05, or 0.02 to 0.35 microns).

One effective sizing method for REVs and MLVs involves extruding an aqueous suspension of the liposomes through a series of polycarbonate membranes having a selected uniform pore size in the range of 0.03 to 0.2 micron, typically 0.05, 0.08, 0.1, or 0.2 microns. The pore size of the membrane corresponds roughly to the largest sizes of liposomes produced by extrusion through that membrane, particularly where the preparation is extruded two or more times through the same membrane. Homogenization methods are also useful for down-sizing liposomes to sizes of 100 nm or less.

The pharmaceutical compositions of the present disclosure can also comprise a pharmaceutically acceptable carrier. Many pharmaceutically acceptable carriers may be employed in the compositions of the present disclosure. Generally, normal saline will be employed as the pharmaceutically acceptable carrier. Other suitable carriers include, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The concentration of lipid structures in the carrier may vary. Generally, the concentration can be about 0.1 to 1000 mg/ml, usually about 1-500 mg/ml, about 5 to 100 mg/ml, etc. Persons of skill may vary these concentrations to optimize treatment with different lipid components or of particular patients.

Subject compositions can include a therapeutically effective in vivo dose of a lipophilic agent (e.g., a wnt protein), and may comprise a cocktail of one or more lipophilic agents (e.g., one or more wnt proteins, one or more Wnt proteins in addition to one or more other lipophilic agents, etc.).

Wnt Signaling Pathway/Wnt Proteins

In some embodiments, the subject agent (e.g., an agent of interest) is a Wnt stimulator agent. A Wnt stimulator agent increases activity of the Wnt signaling pathway in a target cell. A target cell (and/or tissue) that is "Wnt responsive" is a cell/tissue that can respond to the extracellular presence of a Wnt protein by triggering the Wnt signaling pathway. A Wnt responsive cell includes components of the Wnt signaling pathway (described in more detail below), including a receptor (e.g., a Frizzled receptor) that can bind to Wnt proteins. Not all cells are Wnt responsive. In some embodiments, the target cell/tissue is Wnt responsive. In some embodiments the target cell is not Wnt responsive. In some embodiments, it is unknown whether the target cell is Wnt responsive. In some embodiments, it is known whether the target cell is Wnt responsive. In some embodiments, the target cell is part of a heterogeneous population of target cells (i.e., a heterogeneous target cell population) in which some cells are Wnt responsive and some cells are not Wnt responsive (e.g., in some cases a target tissue, such as dental pulp, includes cells that are Wnt responsive as well as cells that are not Wnt responsive). In some embodiments, it is known which cells of a heterogeneous target cell population are Wnt responsive (e.g., stem cells). In some embodiments, it is unknown which cells of a heterogeneous target cell population are Wnt responsive.

The misregulation of Wnt signaling components at various stages during embryogenesis leads to catastrophic developmental defects while misregulation in adults leads to various disease states, including cancer. There are two main branches of the Wnt signaling pathway: (1) the canonical β-Catenin dependent Wnt signaling pathway and (2) the non-canonical β-Catenin independent pathways, which include planar cell polarity (PCP) signaling as well as Calcium signaling (Gao, et. al, Cell Signal. 2010 May; 22(5):717-27. Epub 2009 Dec. 13). As used herein, the terms "Wnt signaling" and "Wnt/β-Catenin signaling" are used interchangeably to refer to the canonical β-Catenin dependent Wnt signaling pathway. As such, a Wnt signaling stimulator, also referred to as a "Wnt stimulator agent" (i.e., agonist) (e.g., Wnt3A) increases output from the β-Catenin dependent Wnt signaling pathway while a Wnt signaling inhibitor (i.e., antagonist) decreases output from the β-Catenin dependent Wnt signaling pathway.

Activation of the Wnt pathway culminates when the protein β-Catenin enters the cell nucleus (for recent review of the canonical β-Catenin dependent Wnt signaling pathway see Clevers et. al., Cell. 2012 Jun. 8; 149(6):1192-205: Wnt/β-catenin signaling and disease). However, in the absence of Wnt signaling, free cytosolic β-Catenin is incorporated into a complex, known in the art as the β-Catenin destruction complex, which includes the proteins Axin, Adenomatous Polyposis Coli (APC), and glycogen synthase kinase (GSK-3β). Phosphorylation of β-Catenin by GSK-3β designates β-Catenin for the ubiquitin pathway and degradation (e.g., via βIRCP).

Transduction of the β-Catenin dependent Wnt signaling pathway (i.e., the Wnt signaling pathway) is triggered by the binding of secreted Wnt ligands to two distinct families of cell-surface receptors: the Frizzled (Fz) receptor family and the LDL-receptor-related protein (LRP) family (Akiyama, Cytokine Growth Factor Rev. 11:273-82 (2000)). This binding leads to the activation of Dishevelled (Dvl) proteins, which inhibit glycogen synthase kinase-3β (GSK-3β) activity (i.e., phosphorylation of β-Catenin), leading to the cytosolic stabilization of β-Catenin. Stabilized β-Catenin then enters the nucleus and associates with the TCF/LEF (T Cell-specific transcription Factor/Lymphoid Enhancer Factor) family of transcription factors to induce transcription of downstream target genes.

In the absence of Wnt signaling, cytosolic (and therefore nuclear) levels of β-Catenin are kept low by negative regulatory components of the pathway while in the presence of Wnt signaling, cytosolic (and therefore nuclear) levels of β-Catenin are stabilized by positive regulatory components of the pathway. For this reason, β-Catenin levels (e.g., monitored via Western blot) can provide insight into whether the Wnt signaling pathway of a cell has been stimulated or inhibited (e.g., increased levels of β-Catenin indicate increased signaling and decreased levels indicate decrease signaling). Likewise, β-Catenin levels in the nucleus (e.g., monitored via fluorescence microscopy, Western blot, etc.) can also be monitored to determine increased or decreased signaling.

By "positive regulatory components" of the Wnt pathway, it is meant proteins that function by enhancing (i.e., stimulating) the Wnt pathway, thus resulting in increased Wnt pathway signaling activity (i.e., increased Wnt pathway signaling output, e.g., increased target gene expression, increased reporter activity, increased levels of β-Catenin, etc.). Examples of known positive regulatory components of the Wnt pathway include, but are in no way limited to: Wnt (secreted, extracellular), Norrin (secreted, extracellular), R-spondin (secreted, extracellular), PORCN, WIs, Frizzled, LRP5 and LRP6, Tspan12, Lgr4, Lgr5, Lgr6, Dvl, β-Catenin, and TCF/LEF. A secreted positive regulatory component of the Wnt pathway (e.g., Wnt, Norrin, R-spondin, and the like) is referred to herein as a "Wnt stimulator polypeptide". In some cases a Wnt stimulator polypeptide is a Wnt protein.

Suitable Wnt polypeptides (i.e., Wnt proteins) include, but are in no way limited to human Wnt polypeptides. Human Wnt proteins of interest in the present application include the following (accession numbers are for mRNAs encoding the associated Wnt protein): Wnt-1 (GenBank Accession No. NM_005430); Wnt-2 (GenBank Accession No. NM_003391); Wnt-2B (Wnt-13) (GenBank Accession No. NM_004185 (isoform 1), NM_024494.2 (isoform 2)), Wnt-3 (RefSeq.: NM_030753), Wnt3a (GenBank Accession No. NM_033131), Wnt-4 (GenBank Accession No. NM_030761), Wnt-5A (GenBank Accession No. NM_003392), Wnt-5B (GenBank Accession No. NM_032642), Wnt-6 (GenBank Accession No. NM_006522), Wnt-7A (GenBank Accession No. NM_004625), Wnt-7B (GenBank Accession No. NM_058238), Wnt-8A (GenBank Accession No. NM_058244), Wnt-8B (GenBank Accession No. NM_003393), Wnt-9A (Wnt-14) (GenBank Accession No. NM_003395), Wnt-9B (Wnt-15) (GenBank Accession No. NM_003396), Wnt-10A (GenBank Accession No. NM_025216), Wnt-10B (GenBank Accession No. NM_003394), Wnt-11 (GenBank Accession No. NM_004626), Wnt-16 (GenBank Accession No. NM_016087)). Although each member has varying degrees of sequence identity with the family, all encode small (i.e., 39-46 kD), acylated, palmitoylated, secreted glycoproteins that contain 23-24 conserved cysteine residues whose spacing is highly conserved (McMahon, A P et al., Trends Genet. 1992; 8: 236-242; Miller, J R. Genome Biol. 2002; 3(1): 3001.1-3001.15). Other Wnt polypeptides of interest in the present invention include orthologs of the above from any mammal, including domestic and farm animals, and zoo, laboratory or pet animals, dogs, cats, cattle, horses, sheep, pigs, goats, rabbits, rats, mice, frogs, zebra fish, fruit fly, worm, etc.

Wnt proteins form a family of highly conserved secreted signaling molecules that regulate cell-to-cell interactions during embryogenesis. The terms "Wnts" or "Wnt gene product" or "Wnt protein" or "Wnt polypeptide" are used interchangeable and encompass native sequence Wnt polypeptides, Wnt polypeptide variants, Wnt polypeptide fragments and chimeric Wnt polypeptides. In some embodiments of the invention, the Wnt protein comprises palmitate covalently bound to a cysteine residue. A "native sequence" polypeptide is one that has the same amino acid sequence as a Wnt polypeptide derived from nature, regardless of the method used for its production. Such native sequence polypeptides can be isolated from cells producing endogenous Wnt protein or can be produced by recombinant or synthetic means. Thus, a native sequence polypeptide can have the amino acid sequence of, e.g. naturally occurring human polypeptide, murine polypeptide, or polypeptide from any other mammalian species, or from non-mammalian species, e.g. *Drosophila, C. elegans*, and the like.

The term "native sequence Wnt polypeptide" includes, without limitation, human and murine Wnt polypeptides. Human Wnt proteins include the following: Wnt1, Genbank reference NP005421.1; Wnt2, Genbank reference NP003382.1, which is expressed in brain in the thalamus, in fetal and adult lung and in placenta; two isoforms of Wnt2B, Genbank references NP004176.2 and NP078613.1. Isoform 1 is expressed in adult heart, brain, placenta, lung, prostate, testis, ovary, small intestine and colon. In the adult brain, it is mainly found in the caudate nucleus, subthalamic nucleus and thalamus. Also detected in fetal brain, lung and kidney. Isoform 2 is expressed in fetal brain, fetal lung, fetal kidney, caudate nucleus, testis and cancer cell lines. Wnt 3 and Wnt3A play distinct roles in cell-cell signaling during morphogenesis of the developing neural tube, and have the Genbank references NP11 0380.1 and X56842 (Swiss-Prot P56704), respectively.

The native human Wnt3A amino acid sequence (NP_149122.1) is specifically disclosed as SEQ ID NO: 19. Wnt 4 has the Genbank reference NP11 0388.2. Wnt 5A and Wnt 5B have the Genbank references NP003383.1 and AK013218. Wnt 6 has the Genbank reference NP006513.1; Wnt 7A has the Genbank reference NP004616.2. Wnt 7B has the Genbank reference NP478679.1. Wnt 8A has two alternative transcripts, Genbank references NP114139.1 and NP490645.1. Wnt 8B has the Genbank reference NP003384.1. Wnt 10A has the Genbank reference NP079492.2. Wnt 10B has the Genbank reference NP003385.2. Wnt 11 has the Genbank reference NP004617.2. Wnt 14 has the Genbank reference NP003386.1. Wnt 15 has the Genbank reference NP003387.1. Wnt 16 has two isoforms, Wnt-16a and Wnt-16b, produced by alternative splicing, Genbank references are NP057171.2 and NP476509.1. All GenBank, SwissProt and other database sequences listed are expressly incorporated by reference herein.

The term "native sequence Wnt protein" or "native sequence Wnt polypeptide" includes the native proteins with or without the initiating N-terminal methionine (Met), and with or without the native signal sequence. The terms specifically include the 352 amino acids long native human Wnt3a polypeptide, without or without its N terminal methionine (Met), and with or without the native signal sequence.

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active Wnt variant will have an amino acid sequence having at least about 90% amino acid sequence identity with a native sequence Wnt polypeptide, preferably at least about 95%, more preferably at least about 99%.

A "chimeric" Wnt polypeptide is a polypeptide comprising a Wnt polypeptide or portion (e.g., one or more domains) thereof fused or bonded to heterologous polypeptide. The chimeric Wnt polypeptide will generally share at least one biological property in common with a native sequence Wnt polypeptide. Examples of chimeric polypeptides include immunoadhesins, combine a portion of the Wnt polypeptide with an immunoglobulin sequence, and epitope tagged polypeptides, which comprise a Wnt polypeptide or portion thereof fused to a "tag polypeptide". The tag polypeptide has enough residues to provide an epitope against which an antibody can be made, yet is short enough such that it does not interfere with biological activity of the Wnt polypeptide. Suitable tag polypeptides generally have at least six amino acid residues and usually between about 6-60 amino acid residues.

A "functional derivative" of a native sequence Wnt polypeptide is a compound having a qualitative biological property in common with a native sequence Wnt polypeptide. "Functional derivatives" include, but are not limited to, fragments of a native sequence and derivatives of a native sequence Wnt polypeptide and its fragments, provided that they have a biological activity in common with a corresponding native sequence Wnt polypeptide. The term "derivative" encompasses both amino acid sequence variants of Wnt polypeptide and covalent modifications thereof.

One may determine the specific activity of a Wnt protein in a composition by determining the level of activity in a functional assay, for example in an in vitro assay, or after in vivo administration in a test model, e.g. accelerating bone regeneration, upregulation of stem cell proliferation, etc., quantitating the amount of Wnt protein present in a non-functional assay, e.g. immunostaining, ELISA, quantitation on Coomasie or silver stained gel, etc., and determining the ratio of in vivo biologically active Wnt to total Wnt.

The effective dose of the Wnt protein may vary depending on the source, purity, preparation method, etc. Where the Wnt protein is L-Wnt3A, the effective dose is usually at least 0.1 µg/ml, at least 0.5 µg/ml, at least 1 µg/ml, at least 2.5 µg/ml, at least 5 µg/ml, at least 7.5 µg/ml, at least 10 µg/ml, at least 15 µg/ml, and may be at least 25 µg/ml, at least 50 µg/ml, or at least 100 µg/ml.

As discussed above, in some embodiments, a Wnt protein (e.g., Wnt3A, e.g., human Wnt3A) is inserted in the non-aqueous phase of a lipid structure, e.g. in the surface of a liposome, micelle, lipid raft, etc., in an emulsion, and the like. In some embodiments the Wnt protein is presented in its active conformation on an outer liposome membrane or micelle. Where the lipid structure is a liposome it can be desirable that the Wnt protein not be encapsulated within the liposome, e.g. in an aqueous phase. The lipid-containing particles typically display the Wnt protein, the particles comprising at least one copy of a wnt protein bearing at least one lipid moiety, where the composition contains at least 50% of the Wnt polypeptides displayed on the exterior surface of the particle. In some cases, R-spondin can be included in the aqueous core of a liposomal WNT3A (L-Wnt3A) and in so doing, amplify and extend the Wnt dependent activation of pulp cells.

For example, see Dhamdhere et al., PLoS One. 2014 Jan. 6; 9(1):e83650; and Zhao et al., Methods Enzymol. 2009; 465:331-47, both of which are hereby incorporated by reference in their entirety.

A subject Wnt stimulator agent is any molecule (e.g., a chemical compound; a non-coding nucleic acid, e.g., a non-coding RNA; a polypeptide; a nucleic acid encoding a polypeptide, etc.) that results in increased output (i.e., increased target gene expression) from the Wnt signaling pathway. For example, a Wnt stimulator agent can function by stabilizing, enhancing the expression of, or enhancing the function of a positive regulatory component of the pathway or by destabilizing, decreasing the expression of, or inhibiting the function of a negative regulatory component of the pathway. Thus, a Wnt stimulator agent can be a positive regulatory component of the pathway (e.g., a Wnt protein), or a nucleic acid encoding one or more positive regulatory components of the pathway. A Wnt stimulator agent can also be a small molecule or nucleic acid that stabilizes a positive regulatory component of the pathway either at the level of mRNA or protein.

In some embodiments, a Wnt stimulator agent functions by stabilizing β-Catenin, thus allowing nuclear levels of β-Catenin to rise. β-Catenin can be stabilized in multiple different ways. As multiple different negative regulatory components of the Wnt signaling pathway function by facilitating the degradation of β-Catenin, a subject Wnt stimulator agent can be a small molecule or nucleic acid inhibitor (e.g., microRNA, shRNA, etc.)(functioning at the level of mRNA or protein) of a negative regulatory component of the pathway. For example, in some embodiments, the Wnt stimulator agent is an inhibitor of GSK-3β. In some such embodiments, the inhibitor of GSK-3β is a small molecule chemical compound (e.g., TWS119, BIO, CHIR-99021, SB 216763, SB 415286, CHIR-98014 and the like).

TWS119: 3-(6-(3-aminophenyl)-7H-pyrrolo[2,3-d]pyrimidin-4-yloxy)phenol is described by Ding et. al, Proc Natl Acad Sci USA. 2003 Jun. 24; 100(13):7632-7. BIO: 6-bromo-3-[(3E)-1,3-dihydro-3-(hydroxyimino)-2H-indol-2-ylidene]-1,3-dihydro-(3Z)-2H-indol-2-one or (2'Z,3E)-6-Bromoindirubin-3'-oxime is described by Meijer et. al, Chem Biol. 2003 December; 10(12):1255-66. CHIR-99021: 6-[[2-[[4-(2,4-dichlorophenyl)-5-(5-methyl-1H-imidazol-2-yl)-2-pyrimidinyl]amino]ethyl]amino]-3-pyridinecarbonitrile is described by Bennett et al., J Biol Chem. 2002 Aug. 23; 277(34):30998-1004. SB 216763: 3-(2,4-dichlorophenyl)-4-(1-methyl-1H-indol-3-yl)-1H-pyrrole-2,5-dione is described by Cross et al., J Neurochem. 2001 April; 77(1): 94-102. SB 415286: 3-(3-chloro-4-hydroxyphenylamino)-4-(2-nitrophenyl)-1H-pyrrole-2,5-dione is described by Cross et al., J Neurochem. 2001 April; 77(1):94-102. CHIR-98014: N2-(2-(4-(2,4-dichlorophenyl)-5-(1H-imidazol-1-yl) pyrimidin-2-ylamino)ethyl)-5 nitropyridine-2,6-diamine is described by Ring et al., Diabetes. 2003 March; 52(3):588-95. Each reference is herein specifically incorporated by reference.

In some cases, a Wnt stimulator agent is a lipophilic agent. For those agents above that are not lipophilic, a Wnt stimulator agent can be such an agent conjugated to a lipid moiety.

The effective dose of a Wnt stimulator agent can be at least 0.1 µM, at least 1 µM, at least 2.5 µM, at least 5 µM, and usually not more than 500 µM, not more than 250 µM, not more than 100 µM, or not more than 50 µM.

By "negative regulatory components" of the Wnt pathway, it is meant proteins that function by antagonizing (i.e., inhibiting) the Wnt pathway, thus resulting in decreased pathway output (i.e., decreased Wnt pathway signaling output, e.g., decreased target gene expression, decreased reporter activity, decreased levels of β-Catenin, etc.). Examples of known negative regulatory components of the Wnt pathway include, but are in no way limited to: WIF, sFRP, DKK, Wnt5, Wnt11, Notum, WISE/SOST, Axin, APC, GSK-3β, CK1γ, WTX, and βTrCP. A secreted negative regulatory component of the Wnt pathway is referred to herein as a "Wnt inhibitor polypeptide".

Wnt inhibitor polypeptides (i.e., secreted negative regulatory components of the Wnt signaling pathway) include members of the WIF (Wnt inhibitory factor), sFRP (Secreted Frizzled Related Protein), DKK (Dickkopf), Notum, and WISE/SOST families, which interfere with the appropriate interactions among Wnt, Frizzled, and LRP proteins (Melkonyan et al., 1997, Proc Natl Acad Sci USA 94(25): 13636-41; Moon et al., 1997, Cell 88(6):725-8; Fedi et al., 1999, J Biol Chem 274(27):19465-72; Nusse, 2001, Nature 411(6835):255-6; Clevers et. al., Cell. 2012 Jun. 8; 149(6): 1192-205: Wnt/β-catenin signaling and disease). Although most Wnt polypeptides are Wnt stimulator polypeptides, certain Wnt polypeptides (e.g., Wnt5 and Wnt11) are Wnt inhibitor polypeptides. Wnt5 and Wnt11 have been demonstrated to stimulate non-canonical (non-β-catenin dependent) Wnt signaling and have also been demonstrated to inhibit canonical (β-catenin dependent) Wnt signaling. Thus, the term "Wnt polypeptide" encompasses some Wnt stimulator polypeptides as well as some Wnt inhibitor polypeptides.

The above described agents can be prepared in a variety of ways. For example, a subject Wnt stimulating composition and/or a subject liphophilic agent (e.g., a Wnt protein) agent can be prepared (together or separately): as a dosage unit, with a pharmaceutically acceptable excipient, with pharmaceutically acceptable salts and esters, etc. Compositions can be provided as pharmaceutical compositions.

Pharmaceutical Compositions

Suitable agents can be provided in pharmaceutical compositions suitable for therapeutic use, e.g. for human treatment. In some embodiments, pharmaceutical compositions of the present disclosure include one or more therapeutic entities of the present disclosure (e.g., a subject Wnt stimulating composition and/or a subject lipophilic agent inserted in the non-aqueous phase of a lipid structure) and include a pharmaceutically acceptable carrier, a pharmaceutically acceptable salt, a pharmaceutically acceptable excipient, and/or esters or solvates thereof. In some embodiments, the use of a subject Wnt stimulating composition and/or a subject lipophilic agent inserted in the non-aqueous phase of a lipid structure includes use in combination with another therapeutic agent (e.g., a dentin-stimulating agent, a pulp survival agent, an anti-infection agent, and the like). Therapeutic formulations that include a subject Wnt stimulating composition and/or a subject lipophilic agent inserted in the non-aqueous phase of a lipid structure can be prepared by mixing the agent(s) having the desired degree of purity with a physiologically acceptable carrier, a pharmaceutically acceptable salt, an excipient, and/or a stabilizer (Remington's Pharmaceutical Sciences 16th edition, Osol, A. Ed. (1980)) (e.g., in the form of lyophilized formulations or aqueous solutions). A composition having a subject Wnt stimulating composition and/or a subject lipophilic agent inserted in the non-aqueous phase of a lipid structure can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

"Pharmaceutically acceptable salts and esters" means salts and esters that are pharmaceutically acceptable and have the desired pharmacological properties. Such salts include salts that can be formed where acidic protons present in the compounds are capable of reacting with inorganic or organic bases. Suitable inorganic salts include those formed with the alkali metals, e.g. sodium and potassium, magnesium, calcium, and aluminum. Suitable organic salts include those formed with organic bases such as the amine bases, e.g., ethanolamine, diethanolamine, triethanolamine, tromethamine, N-methylglucamine, and the like. Such salts also include acid addition salts formed with inorganic acids (e.g., hydrochloric and hydrobromic acids) and organic acids (e.g., acetic acid, citric acid, maleic acid, and the alkane- and arene-sulfonic acids such as methanesulfonic acid and benzenesulfonic acid). Pharmaceutically acceptable esters include esters formed from carboxy, sulfonyloxy, and phosphonoxy groups present in the compounds, e.g., $C_{1-6}$ alkyl esters. When there are two acidic groups present, a pharmaceutically acceptable salt or ester can be a mono-acid-mono-salt or ester or a di-salt or ester; and similarly where there are more than two acidic groups present, some or all of such groups can be salified or esterified. Compounds named in this invention can be present in unsalified or unesterified form, or in salified and/or esterified form, and the naming of such compounds is intended to include both the original (unsalified and unesterified) compound and its pharmaceutically acceptable salts and esters. Also, certain compounds named in this invention may be present in more than one stereoisomeric form, and the naming of such compounds is intended to include all single stereoisomers and all mixtures (whether racemic or otherwise) of such stereoisomers.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

In some embodiments, pharmaceutical compositions can include large, slowly metabolized macromolecules such as proteins, polysaccharides such as chitosan, polylactic acids, polyglycolic acids and copolymers (such as latex functionalized Sepharose™, agarose, cellulose, and the like), polymeric amino acids, amino acid copolymers, and lipid aggregates (such as oil droplets or liposomes).

Acceptable carriers, excipients, or stabilizers are non-toxic to recipients at the dosages and concentrations employed, and include buffers such as phosphate, citrate, and other organic acids; antioxidants including ascorbic acid and methionine; preservatives (such as octadecyidimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEEN™, PLURONICS™ or polyethylene glycol (PEG). Formulations to be used for in vivo administration must be sterile. This is readily accomplished by filtration through sterile filtration membranes.

Ingredients may also be entrapped in microcapsule prepared, for example, by coacervation techniques or by interfacial polymerization, for example, hydroxymethylcellulose or gelatin-microcapsule and poly-(methylmethacylate) microcapsule, respectively, in colloidal drug delivery systems (for example, liposomes, albumin microspheres, microemulsions, nano-particles and nanocapsules) or in macroemulsions. Such techniques are disclosed in Remington's Pharmaceutical Sciences 16th edition, Osol, A. Ed. (1980).

Compositions can be prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient. The pharmaceutical compositions can be formulated as sterile, substantially isotonic and in full compliance with all Good Manufacturing Practice (GMP) regulations of the U.S. Food and Drug Administration.

Methods

The present disclosure provides compositions and methods for enhancing dentin production by dental pulp tissue. Such methods can include administering to the pulp of a tooth of an individual, a Wnt stimulating composition that includes a Wnt stimulator agent, at a dose sufficient to enhance the production of dentin by the pulp. In some cases, the pulp is exposed pulp and said administering includes contacting the exposed pulp with the Wnt stimulating composition. In some cases, said administering includes contacting dentin with the Wnt stimulating composition, whereby the Wnt stimulating composition penetrates the dentin to the underlying pulp tissue. As discussed above, the Wnt stimulator agent can be a lipophilic Wnt stimulator agent. In some cases, the Wnt stimulator agent is a Wnt protein (e.g., a Wnt protein having a lipid moiety)(e.g., a Wnt3A protein). In some cases, the Wnt stimulating composition includes a lipophilic Wnt stimulator agent (e.g., a Wnt protein, e.g., having a lipid moiety; a Wnt3A protein, e.g., having a lipid moiety; and the like) inserted in the non-aqueous phase of a lipid structure. Thus, in some cases, a lipophilic agent inserted in the non-aqueous phase of a lipid structure is an L-Wnt (e.g., L-Wnt3A).

The present disclosure provides compositions and methods for delivering a lipophilic agent to pulp tissue of a tooth of an individual. Such methods can include contacting dentin of the tooth (e.g., exposed dentin) with a composition that includes a lipophilic agent inserted in the non-aqueous phase of a lipid structure (e.g., a liposomes, micelles, and the like), whereby the lipophilic agent penetrates the dentin to the underlying pulp tissue. In some cases, the individual has tooth sensitivity. In some cases, the pulp tissue of said tooth is not exposed. In some cases, the pulp tissue of said tooth is exposed. In some cases, the method includes, prior to contacting the dentin, a step of exposing the dentin. In some cases, the lipophilic agent is a growth factor (e.g., a growth factor having a lipid moiety). In some cases, the lipophilic agent is a lipophilic Wnt stimulator agent. In some cases, the Wnt stimulator agent is a Wnt protein (e.g., a Wnt protein having a lipid moiety)(e.g., a Wnt3A protein). Thus, in some cases, a lipophilic agent inserted in the non-aqueous phase of a lipid structure is an L-Wnt (e.g., L-Wnt3A).

In some cases, the method includes, prior to contacting dentin (e.g., prior to contacting dentin with a composition having a lipophilic agent inserted in the non-aqueous phase of a lipid structure), a step of exposing dentin. For example, when practicing a subject method, (e.g., as part of a dental procedure), existing metal or plastic restorations, carious dentin, or other medicants (e.g., pulp-lining materials) can be removed, thus exposing dentin. In some cases, exposed dentin is cleaned (e.g, with a mild solvent such as ethylenediaminetetraacetic acid (EDTA), e.g., 15-17%) prior to contacting the dentin, e.g., to remove a smear layer. In some cases, the dentin surface can be rinsed prior contacting the dentin (e.g., prior to contacting the dentin with a composition comprising a lipophilic agent inserted in the non-aqueous phase of a lipid structure). In some cases, the dentin surface can be rinsed and then gently air-dried prior to contacting dentin (e.g., prior to contacting the dentin with a composition comprising a lipophilic agent inserted in the non-aqueous phase of a lipid structure). In some cases, (e.g., after removal of decayed enamel, and for example if the preparation extends into the dentin), a subject composition having a lipophilic agent inserted in the non-aqueous phase of a lipid structure (e.g, L-Wnt, L-Wnt3A, and the like) may be applied to the dentin (e.g., the dentin can be contacted with the subject composition) to stimulate pulp cells to produce additional dentin.

Figure 7:
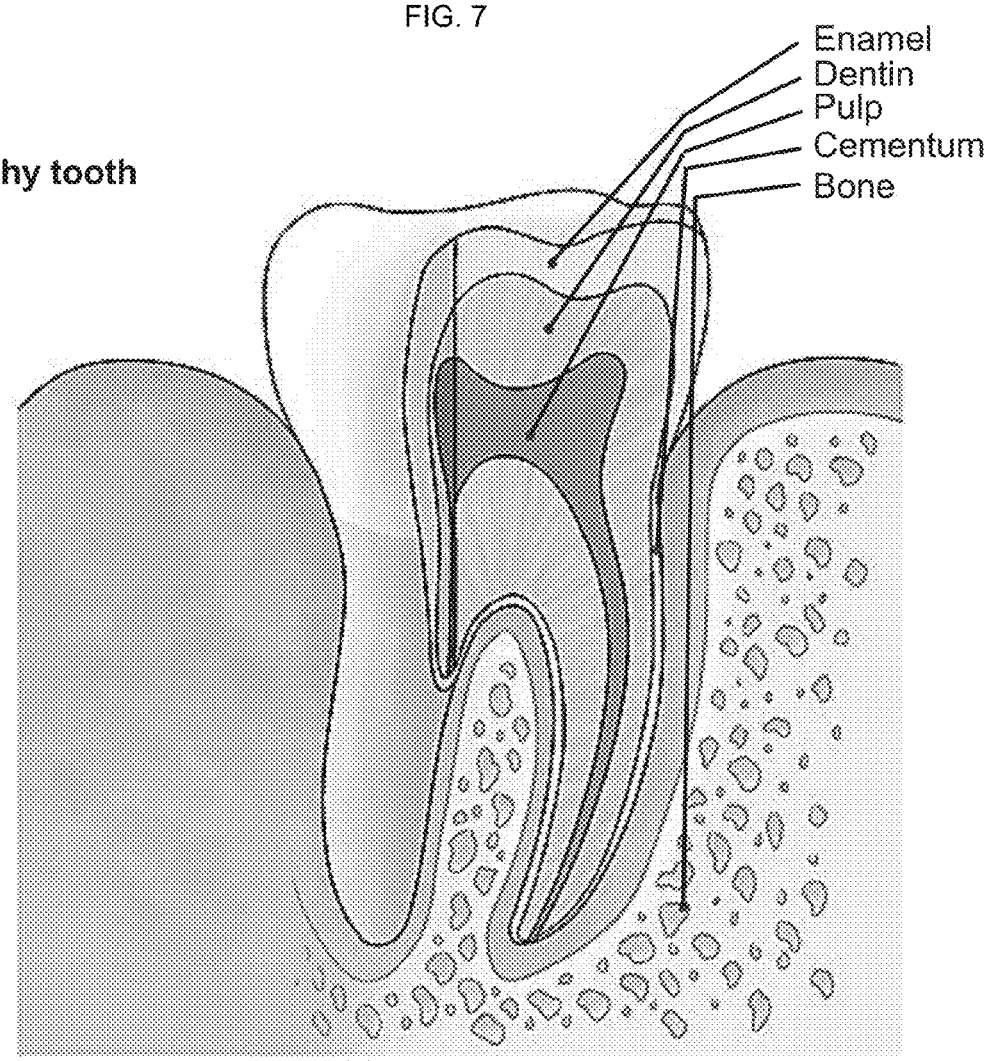
FIG. 7. A schematic representation of a healthy tooth (top) and a tooth in which the pulp is exposed (bottom).
Figure 7:
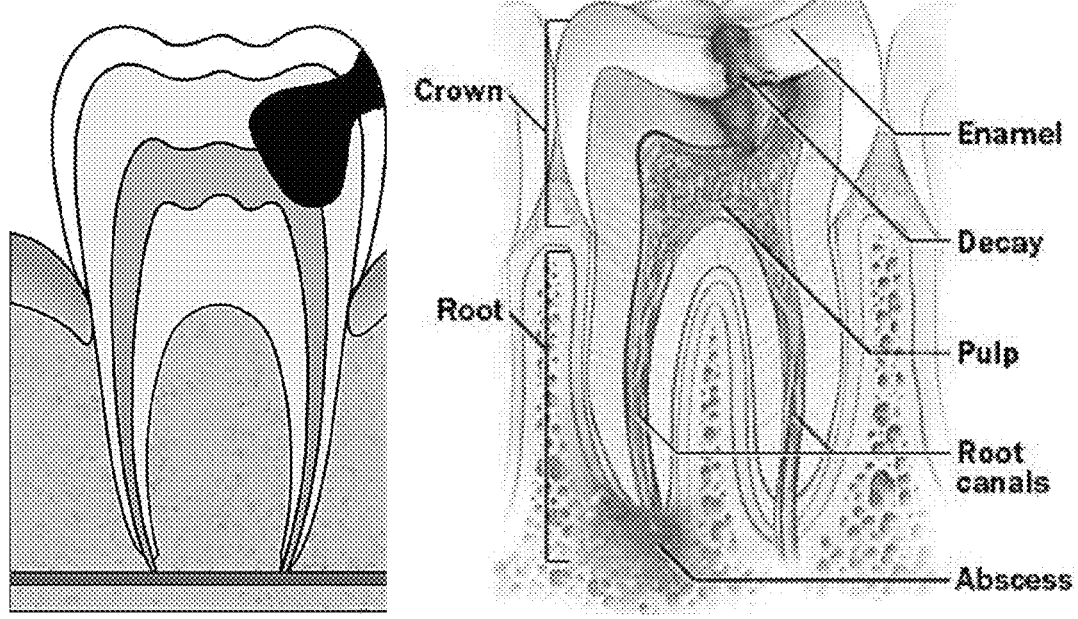

In some cases, the individual (e.g., the individual to be treated using the subject methods and/or compositions) has tooth sensitivity. When an individual has sensitive teeth, certain activities, such as brushing, flossing, eating and drinking, can cause sharp, temporary pain in the teeth. Sensitive teeth can be the result of worn tooth enamel or exposed tooth roots. Tooth sensitivity can be caused by factors such as a cavity, a carious lesion, a cracked or chipped tooth, a recently placed filling or a side effect of other dental procedures (e.g., dental restoration, bleaching, and the like), periodontal disease, and/or as a result of aging. In some cases, the pulp of the tooth to be treated is exposed (e.g., via chipping, cavity, a dental procedure, etc.)(e.g., see FIG. 7). In some cases, the pulp of the tooth to be treated is not exposed. In some cases, the individual (e.g., the individual to be treated using the subject methods and/or compositions) has one or more of: a cavity, a carious lesion, a cracked or chipped tooth, a recently placed filling, a side effect of a dental procedure (e.g., dental restoration, bleaching, and the like), and periodontal disease.

For example, in some cases, a carious lesion may appear (e.g., radiographically appear) to be near or to impinge upon the pulp cavity. The subject methods (e.g., the application of L-WNT3A) can be used to activate stem cells, progenitor cells, and/or odontoblasts within the viable pulp cavity and in doing so stimulate/enhance dentin formation. The dentin can act as an insulator and can protect the remaining pulp tissue (e.g., from trauma).

In some cases, pulp tissue of a tooth is exposed and the method is a method of administering to the pulp of the tooth of an individual, a Wnt stimulating composition that includes a Wnt stimulator agent, at a dose sufficient to enhance the production of dentin by the pulp. In some cases, the pulp tissue can be exposed due to injury, a carious lesion, etc. (e.g., a chipped tooth, a cavity, and the like). In some cases, the pulp tissue can be exposed intentionally (e.g., by a person performing a dental procedure). For example, the pulp tissue can be exposed during a preparation of the tooth for the subject methods, and/or for some other dental procedure. In some cases, a subject method includes a step of exposing pulp of a tooth to produce the exposed pulp. In some cases, the administering includes contacting the exposed pulp with a Wnt stimulating composition, which includes Wnt stimulator agent. In some cases, the Wnt stimulator agent is a lipophilic Wnt stimulator agent. In some cases, the Wnt stimulator agent is a Wnt protein (e.g., a Wnt protein having a lipid moiety)(e.g., a Wnt3A protein, e.g., having a lipid moiety). In some cases, the Wnt stimulating composition includes a lipophilic Wnt stimulator agent (e.g., a Wnt protein, e.g., having a lipid moiety; a Wnt3A protein, e.g., having a lipid moiety; and the like) inserted in the non-aqueous phase of a lipid structure. Thus, in some cases, a Wnt stimulating composition includes L-Wnt (e.g., L-Wnt3A). In some cases, the pulp tissue can be exposed unintentionally (e.g., by a person performing a dental procedure).

The terms "treatment", "treating", "treat" and the like are used herein to generally refer to obtaining a desired pharmacologic and/or physiologic effect. The effect can be prophylactic in terms of completely or partially preventing a disease or symptom(s) thereof and/or may be therapeutic in terms of a partial or complete stabilization or cure for a disease and/or adverse effect attributable to the disease. The subject methods are useful for both prophylactic and therapeutic purposes. Thus, as used herein, the term "treating" is used to refer to both treatment of a pre-existing condition (e.g., tooth sensitivity, pulp exposure, and the like), and to preventative treatments (e.g., to increase dentin of a tooth prior to symptoms associated with reduced dentin; e.g., as a way to prevent, reduce the likelihood of, or reduce the severity of future tooth sensitivity following a dental procedure). Evidence of therapeutic effect may be any diminution in the severity of the condition relative to the pre-existing condition or relative to the expected outcome in the absence of treatment. The therapeutic effect can be measured in terms of clinical outcome or can be determined by immunological or biochemical tests (e.g., tests to determine if Wnt signaling activity was induced). Individuals to be treated can be mammals, e.g. primates, including humans, may be laboratory animals, e.g. rabbits, rats, mice, etc., particularly for evaluation of therapies, horses, dogs, cats, farm animals, etc.

A therapeutic treatment is one in which the subject is inflicted prior to administration and a prophylactic treatment is one in which the subject is not inflicted prior to administration. In some embodiments, the subject has an increased likelihood of becoming inflicted or is suspected of being inflicted prior to treatment. In some embodiments, the subject is suspected of having an increased likelihood of becoming inflicted.

As used herein, the term "pulp exposure" or "dental pulp exposure" refers to exposure of the dental pulp tissue. In healthy teeth, pulp resides within the dentin (e.g., see FIG. 7), but pulp exposure can lead to inflammation, infection, abscess formation, etc. Pulp exposure can result from traumatic injury (e.g., a cracked tooth), decay, cavity formation, and the like. In some cases, pulp is exposed during (e.g., as a result of) a dental procedure (which may be intentional or unintentional exposure). Pulp exposure can be acute (e.g., a cracked tooth), or can occur over a period of time (e.g., via formation of a cavity). In some cases, a subject method includes a step of exposing pulp of a tooth prior to contacting the pulp with a subject Wnt stimulatory composition.

In some cases, the subject methods are performed after placement of a deep restoration (amalgam, composite resin, crown) that radiographically appears to be near to, or impinges upon, the pulp cavity. In some cases, the subject methods are performed after direct pulp capping in young patients, or in patients in which the pulp cavity is inadvertently exposed. In some cases, the subject methods are performed after placement of any tooth restoration (amalgam, composite resin, crown), to prevent and/or to reduce the likelihood of tooth sensitivity. In some cases, a subject Wnt stimulating composition is topically applied to root surfaces after root planning and scaling for periodontal disease patients. In some cases, a subject Wnt stimulating composition (e.g., L-Wnt, L-Wnt3A, and the like) is applied to teeth with incipient carious lesions for which removal of the decayed enamel is generally considered sufficient. All of the methods described herein have broad applications in general restorative dentistry, prosthodontics, and periodontics.

In some cases, the subject methods are a treatment of sensitive teeth (tooth sensitivity), e.g., caused by a dental restoration, a carious lesion, periodontal disease, or as a result of aging. For example, in teeth where a carious lesion radiographically appears to be near to or impinges upon the pulp cavity, the application of a subject composition (e.g., L-WNT3A) can be used to activate stem cells, progenitor cells, and/or odontoblasts within the viable pulp cavity and in doing so stimulate tertiary dentin formation. This tertiary dentin can act as an insulator and protects the remaining pulp tissue from trauma.

In some cases, a Wnt stimulating composition and/or a lipophilic agent (e.g., a Wnt protein, such as Wnt3A) inserted in the non-aqueous phase of a lipid structure (e.g., L-WNT3A) is applied to the dentin (or in some cases applied to exposed pulp). In other words, in some cases, dentin and/or exposed pulp is contacted with a Wnt stimulating composition and/or a lipophilic agent (e.g., a Wnt protein, such as Wnt3A) inserted in the non-aqueous phase of a lipid structure. A subject composition can be re-applied over the course of 1 to 30 minutes (e.g., 1 to 15 minutes, 2 to 15 minutes, 2 to 12 minutes, 4 to 15 minutes, 4 to 12 minutes, 5 to 15 minutes, 5 to 12 minutes, 5 to 10 minutes, 7 to 15 minutes, 7 to 12 minutes, or 8 to 12 minutes). In some cases, after contacting the denting and/or exposed pulp with a subject composition, the tooth is closed using standard tooth replacement materials (composite resin, amalgam, glass ionomer cement, etc). In some cases, a subject method includes a step of closing the tooth. In some cases, dentin and/or exposed pulp is contacted with a subject composition two more times (e.g, 3 or more times, 4 or more times, 5 or more times) over a period of time in a range of from 1 to 30 minutes (e.g., 1 to 15 minutes, 2 to 15 minutes, 2 to 12 minutes, 4 to 15 minutes, 4 to 12 minutes, 5 to 15 minutes, 5 to 12 minutes, 5 to 10 minutes, 7 to 15 minutes, 7 to 12 minutes, or 8 to 12 minutes).

The dosage of the therapeutic formulation will vary widely, depending upon the nature of the condition, the frequency of administration, the manner of administration, the clearance of the agent from the host, and the like. The initial dose can be larger, followed by smaller maintenance doses. The dose can be administered as infrequently as weekly or biweekly, or more often fractionated into smaller doses and administered daily, semi-weekly, or otherwise as needed to maintain an effective dosage level.

In some embodiments, administration of a subject composition (e.g., a wnt stimulator composition, a composition that includes a lipohilic agent, etc.) is performed by local administration. Local administration, as used herein, may refer to topical administration, but can also refer to injection or other introduction into the body at a site of treatment (e.g., at or near the sight of a dental injury, tooth sensitivity, etc.).

In some embodiments, a subject composition is administered on a short term basis, for example a single administration, or a series of administration performed over, e.g. 1, 2, 3 or more days, up to 1 or 2 weeks. The size of the dose administered can be determined by a physician and will depend on a number of factors, such as the nature and gravity of the disease, the age and state of health of the patient and the patients tolerance to the procedure and/or to the composition.

The terms "co-administration", "co-administer", and "in combination with" include the administration of two or more therapeutic agents (e.g., a subject Wnt stimulating composition and/or a subject lipophilic agent inserted in the non-aqueous phase of a lipid structure; and/or another dentin-stimulating agent, a pulp survival agent, an anti-infection agent, and the like) either simultaneously, concurrently or sequentially within no specific time limits. In one embodiment, the agents are contacted with the target tissue (e.g., pulp and/or dentin) or in the subject's body at the same time or exert their biological or therapeutic effect at the same time. In some embodiments, the therapeutic agents are in the same composition or unit dosage form. In some embodiments, the therapeutic agents are in separate compositions or unit dosage forms. In certain embodiments, a first agent can be administered prior to (e.g., minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent.

In some cases, a subject Wnt stimulating composition and/or a subject lipophilic agent inserted in the non-aqueous phase of a lipid structure (e.g., formulated as a pharmaceutical composition) is co-administered with one or more additional agents (e.g., a dentin-stimulating agent, a pulp survival agent, an anti-infection agent, and/or a growth factor, etc.). Such administration may involve concurrent (i.e. at the same time), prior, or subsequent administration of the additional agent with respect to the administration of an agent or agents of the disclosure. In some embodiments, treatment is accomplished by administering a combination (co-administration) of a subject Wnt stimulating composition and/or a subject lipophilic agent inserted in the non-aqueous phase of a lipid structure with another agent (e.g., a dentin-stimulating agent, a pulp survival agent, an anti-infection agent, and/or a growth factor, etc.).

Treatment may be combined with other active agents, such as antibiotics, cytokines, etc. Classes of antibiotics include penicillins, e.g. penicillin G, penicillin V, methicillin, oxacillin, carbenicillin, nafcillin, ampicillin, etc.; penicillins in combination with β-lactamase inhibitors, cephalosporins, e.g. cefaclor, cefazolin, cefuroxime, moxalactam, etc.; carbapenems; monobactams; aminoglycosides; tetracyclines; macrolides; lincomycins; polymyxins; sulfonamides; quinolones; cloramphenical; metronidazole; spectinomycin; trimethoprim; vancomycin; etc. Cytokines may also be included, e.g. interferon γ, tumor necrosis factor α, interleukin 12, etc.

A "therapeutically effective dose" or "therapeutic dose" is an amount sufficient to effect desired clinical results (i.e., achieve therapeutic efficacy). A therapeutically effective dose can be administered in one or more administrations. For purposes of this disclosure, a therapeutically effective dose of a subject Wnt stimulating composition and/or a subject lipophilic agent inserted in the non-aqueous phase of a lipid structure is an amount that is sufficient to palliate, ameliorate, stabilize, reverse, prevent, slow or delay the progression of the disease and/or injury state (e.g., pulp exposure, tooth sensitivity, etc.). Thus, a therapeutically effective dose of a subject Wnt stimulating composition and/or a subject lipophilic agent inserted in the non-aqueous phase of a lipid structure can increase the amount of dentin produced by the tooth pulp, can decrease cell death in the tooth pulp (e.g., which can be detected using techniques such as TUNEL staining, Casp8 expression, CASPASE 3 expression, and the like); can increase cell proliferation in the tooth pulp (e.g., which can be detected using techniques such as Ki67 immunostaining, BrdU incorporation, and the like); can increase the number of differentiated odontoblasts in the tooth pulp (e.g., which can be detected using expression markers such as Nestin and/or the extracellular matrix protein DSP); can increase levels of highly organized tubular dentin matrix in the tooth pulp; and can increase levels of a collagenous matrix with a linear organization (suggestive of tubular orthodentin) in the tooth pulp (e.g., as can be detected by picrosirius red staining and polarized light).

As such, in some cases, the subject methods include a step of evaluating tooth pulp for increased dentin produced by the tooth pulp, decreased cell death in the tooth pulp (e.g., which can be detected using techniques such as TUNEL staining, Casp8 expression, CASPASE 3 expression, and the like); increased cell proliferation in the tooth pulp (e.g., which can be detected using techniques such as Ki67 immunostaining, BrdU incorporation, and the like); increased number of differentiated odontoblasts in the tooth pulp (e.g., which can be detected using expression markers such as Nestin and/or the extracellular matrix protein DSP); increased levels of highly organized tubular dentin matrix in the tooth pulp; and/or increased levels of a collagenous matrix with a linear organization (suggestive of tubular orthodentin) in the tooth pulp (e.g., as can be detected by picrosirius red staining and polarized light). The "increase" and/or "decrease" can be relative to any convenient control (e.g., a pre-determined value, an untreated control tooth, a sample from the same patient evaluated prior to treatment; a control treated with a placebo (e.g., a saline solution); and the like).

In some cases, the subject methods include a step of evaluating whether a treatment stimulated (e.g., increased) Wnt signaling (i.e., activity of the Wnt signaling pathway). Any convenient method can be used to detect such activity (e.g., expression of a target gene of the Wnt signaling pathway, increase of a Wnt reporter, etc.). The "increase" and/or "decrease" can be relative to any convenient control (e.g., a pre-determined value, an untreated control tooth, a sample from the same patient evaluated prior to treatment; a control treated with a placebo (e.g., a saline solution); and the like).

It will be understood by one of skill in the art that guidelines for parameters such as dosage and frequency can be adjusted for various factors such as molecular weight of the active agent, type of administration, e.g. intranasal, inhalation, topical, injection, systemic (e.g. i.m., i.p., i.v.), and the like. A subject composition/agent can be administered by any suitable means, including topical, oral, parenteral, intrapulmonary, and intranasal. Parenteral infusions include intramuscular, intravenous (bolus or slow drip), intraarterial, intraperitoneal, intrathecal or subcutaneous administration. Administration may include injection, parenteral routes such as intravenous, intravascular, intraarterial, subcutaneous, intramuscular, intratumor, intraperitoneal, intraventricular, intraepidural, or others as well as oral, nasal, ophthalmic, rectal, or topical. Sustained release administration is also specifically included in the disclosure (e.g., such as depot injections or erodible implants). Localized delivery is contemplated, e.g., topical administration to dentin and/or contact with exposed pulp tissue.

As noted above, a subject composition/agent can be formulated with a pharmaceutically acceptable carrier (one or more organic or inorganic ingredients, natural or synthetic, with which a subject agent is combined to facilitate its application). A suitable carrier includes sterile saline although other aqueous and non-aqueous isotonic sterile solutions and sterile suspensions known to be pharmaceutically acceptable are known to those of ordinary skill in the art. An "effective amount" refers to that amount which is capable of ameliorating or delaying progression of the diseased, degenerative or damaged condition. An effective amount can be determined on an individual basis and will be based, in part, on consideration of the symptoms to be treated and results sought.

Kits

Also provided are kits for use in the methods (e.g., pharmaceutical pack or kit including one or more containers having one or more of the ingredients of the pharmaceutical compositions of the invention. The subject kits can include a Wnt stimulating composition that includes a Wnt stimulator agent (e.g., at a dose sufficient to enhance the production of dentin by dental pulp) and/or a lipophilic agent inserted in the non-aqueous phase of a lipid structure. In some cases, a Wnt stimulator agent is a lipophilic agent inserted in the non-aqueous phase of a lipid structure. In some embodiments, a kit comprises two or Wnt stimulator agents and/or two or more lipophilic agents inserted in the non-aqueous phase of a lipid structure (e.g., two or more lipophilic agents each inserted in the non-aqueous phase of separate lipid structures; and/or two or more lipophilic agents inserted in the non-aqueous phase of the same lipid structure). In some embodiments, a Wnt stimulator agent and/or a lipophilic agent inserted in the non-aqueous phase of a lipid structure is provided in a dosage form (e.g., a therapeutically effective dosage form). In the context of a kit, a Wnt stimulator agent and/or a lipophilic agent inserted in the non-aqueous phase of a lipid structure can be provided in liquid or sold form in any convenient packaging (e.g., stick pack, dose pack, etc.). The agents of a kit can be present in the same or separate containers. For example, a kit may have a Wnt stimulator agent in one container and in another container, a lipophilic agent inserted in the non-aqueous phase of a lipid structure. As another example, a kit may have a Wnt stimulator agent in one container and in another container, another Wnt stimulatory agent. As yet another example, a kit may have in one container a lipophilic agent inserted in the non-aqueous phase of a lipid structure, and in another container, a different a lipophilic agent inserted in the non-aqueous phase of a lipid structure. In some cases, the agents of a subject kit are present in the same container. The above kits may include a reagent and/or component for a dental procedure associated with the subject methods (e.g., a reagent and/or component for capping a tooth, for exposing dentin, for exposing pulp, and the like).

In addition to the above components, the subject kits may further include (in certain embodiments) instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, and the like. Yet another form of these instructions is a computer readable medium, e.g., diskette, compact disk (CD), flash drive, and the like, on which the information has been recorded. Yet another form of these instructions that may be present is a website address which may be used via the internet to access the information at a removed site.

The invention now being fully described, it will be apparent to one of ordinary skill in the art that various changes and modifications can be made without departing from the spirit or scope of the invention.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

EXAMPLES

Example 1

The experiments below show a liposome-reconstituted form of WNT3A produces a stable form of the protein that when used as a biomimetic compound activates cells in the injured tooth pulp, stimulating dentin regeneration. A Wnt-amplified environment was found to be associated with superior pulp healing after pulp injury, for example, the number of cells undergoing apoptosis was significantly reduced, resulting in significantly better survival of injured odontoblasts and an increase in tertiary dentin. Pulp cells responded to elevated Wnt stimulus by differentiating into dentin-secreting odontoblasts. Thus, transiently amplifying a Wnt response resulted in improved pulp vitality.

Materials and Methods

Animals

The Stanford Committee on Animal Research and the Animal Care Committee of the University Paris Descartes (agreement CEEA34.CC.016.11, Comité d'éthique pour l'expérimentation animale no. 34, Paris, France) approved all experimental procedures. Rats were purchased from Janvier Labs. $Axin2^{LacZ/LacZ}$ (#11809809) and $Axin2^{CreERT2/+}$; $R26R^{mTmG/+}$ (#018867 and #007576, respectively) mice were purchased from Jackson Labs. For $Axin2^{CreERT2/+}$; $R26R^{mTmG/+}$ mice, tamoxifen was delivered IP (4.0 mg/25 mg body weight) for 5 consecutive days.

Animal Surgeries

Adult male mice (3-5 months old) were anesthetized with an intraperitoneal injection of ketamine (80 mg/kg) and xylazine (16 mg/kg). In total, 72 mice (36 $Axin2^{LacZ/+}$ and 36 $Axin2^{LacZ/LacZ}$ mice) were used. A cavity was created with a Ø 0.3 mm diameter round bur (E0123, Dentsply Maillefer, Ballaigues, Switzerland) then a #6 k-file was used to expose the dental pulp. Glass ionomer cement (3M) was used to cap the injury. Mice were sacrificed at times indicated in the experiments.

In rats, a cavity was created with a Ø 0.2-mm-diameter round bur then a root-canal-shaping rotary nickel-titanium file system (Protaper, Dentsply) was used to expose the dental pulp. After pulp exposure, beads treated either with L-WNT3A (N=18), or L-PBS (N=18) were implanted into the pulp chamber using a blunt steel probe (see below for details on the preparation of the beads). Biodentine cement (Septodont, Saint-Maur des Fosse's, France) was used to cap the injury. Rats were sacrificed at times indicated in the experiments.

Preparation and Delivery of L-WNT3A

Purified recombinant human WNT3A protein was incubated with liposome vesicles as described (13). L-WNT3A (10 ng, see (14)) or L-PBS (N=18 for each condition) was delivered on Affi-Gel agarose beds (Bio-Rad Laboratories) that had been soaked overnight at 37° C. in the relevant solutions (15).

Sample Preparation, Processing, Histology, Histomorphometrics, and Cellular Assays Maxillae were harvested, the skin and outer layers of muscle were removed, and the tissues were fixed. Tissues were sectioned at a thickness of 8 μm and processed using established procedures (16). Histologic staining was performed as described (16). A minimum of six sections were used to quantify the amount of new dentin. Histomorphometric measurements were performed as described (17).

X-gal staining was performed as described (18). TUNEL staining was performed as described by the manufacturer (In Situ Cell Death Detection Kit, Roche). Immunostaining was performed using standard procedures (10). For cell proliferation analysis, BrdU labeling reagent (Invitrogen, Carlsbad, Calif.) was either injected IP, or added to culture media according to the manufacturer's instructions; animals were sacrificed 12 hours later and both bone marrow-derived stem cells and dental pulp cells were fixed 12 hours later.

Primary antibodies and their dilutions were as follows: anti-biotinylated BrdU (1:200), anti-Nestin (1:300), anti-Ki67 (1:200), anti-PCNA (1:1000), anti-DSP (1:1000).

Dental Pulp Stem Cells and Bone Marrow Treatments

Human dental pulp stem cells were isolated as described (19), in accordance with the Ethics committee of the Pirkanmaa Hospital District, Tampere, Finland (R06009). Cells were cultured in Dulbecco modified Eagle Medium (DMEM) containing Nutrient Mixture F-12 with 10% fetal bovine serum. Cells were treated with L-PBS or L-WNT3A (effective concentration=0.06 μg/mL) at 37° C. for 6, 12, and 24 hours. RNA was isolated afterwards and analyzed by qRT-PCR (see below) and BrdU incorporation (below).

Bone marrow was harvested from the femora and tibiae of adult mice, aliquoted to produce similar sized samples. DNA content was measured to ensure that variation between samples was <10% (20). Each aliquot was incubated with 20

μL of DMEM with 10% fetal bovine serum containing L-PBS or L-WNT3A (effective concentration=0.15 μg/mL) at 37° C. for 4 hours. RNA was isolated afterwards and analyzed by qRT-PCR, or the tissues were fixed in 4% PFA at 4° C. then processed into OCT for cryosectioning. TUNEL activity and Ki67 expression were analyzed using 10 μm sections (see above).

Quantitative RT-PCR

Total RNA was extracted using TRIzol (Invitrogen). cDNA was synthesized by using SuperScript III First-Strand Synthesis Kit (Invitrogen) according to the instructions of the manufacturer. RT-PCR and quantitative PCR (ABI Prism 7900 HT Sequence Detection System) were performed as described (10). All reactions were performed in triplicate.

The following primer sets were used:

```
Axin2,
                                        (SEQ ID NO: 1)
5'-ACCCTGGGCCACTTTAAAG-3' (sense)
and (SEQ ID NO: 2)
5'-CCTTCATACATCGGGAGCAC-3' (antisense);

Axin2 exon 1,
                                        (SEQ ID NO: 3)
5'-TCAGTAACAGCCCAAGAACC-3' (sense)
and (SEQ ID NO: 4)
5'-GAGCCTCCTCTCTTTACAGC-3' (antisense);

CASP3,
                                        (SEQ ID NO: 5)
5'-GCACTGGAATGTCATCTCGCT-3' (sense)
and (SEQ ID NO: 6)
5'-GGCCCATGAATGTCTCTCTGAG-3' (antisense);

Lef1,
                                        (SEQ ID NO: 7)
5'-ACACCCTGATGAAGGAAAGC-3' (sense)
and (SEQ ID NO: 8)
5'-GACCCATTTGACATGTACGG-3' (antisense);

PCNA,
                                        (SEQ ID NO: 9)
5'-CTTGGAATCCCAGAACAGGA-3' (sense)
and (SEQ ID NO: 10)
5'-CAGCATCTCCAATGTGGCTA-3 (antisense);

Nestin:
                                        (SEQ ID NO: 11)
5'-CTCGGGAGAGTCGCTTAGAG-3' (sense)
and (SEQ ID NO: 12)
5'-CACAGCCAGCTGGAACTTT-3' (antisense);

Dentin sialophosphoprotein (DSPP):
                                        (SEQ ID NO: 13)
5'-GGAATGGAGAGAGGACTGCT-3' (sense)
and (SEQ ID NO: 14)
5'-AGGTGTTGTCTCCGTCAGTG-3' (antisense);

Osteocalcin:
                                        (SEQ ID NO: 15)
5'-TGTGACGAGCTATCAAACCAG-3' (sense)
and
```

```
                                        (SEQ ID NO: 16)
5'-GAGGATCAAGTTCTGGAGAGC-3' (antisense);
and Collagen type I:
                                        (SEQ ID NO: 17)
5'-AAGGACAAGAGGCACGTCTG-3' (sense)
and (SEQ ID NO: 18)
5'-CGCTGTTCTTGCAGTGGTAG-3' (antisense).
```

Dentin Volume and Mineral Density Micro-CT Analysis

Micro-computed topographies of the maxillae were performed using a SkyScan 1176 scanner (SkyScan, Bruker, Belgium) at a 5 μm resolution. Scanning was done at 45 kV, 556 mA. Reconstruction of sections was achieved using a modified Feldkamp cone-beam algorithm with beam hardening correction set to 50%. CTAnalyzer software (version 1.02; SkyScan) was employed for morphometric quantification.

Reparative Dentin Histomorphometry

Sections from rat molars were examined morphometrically at a constant magnification (250×) with a semi-automatic image analyzer coupling the microscope to a video camera and a computer (21). Six sections per sample (N=6 molars per group) were taken at the center of the pulp exposure site. At day 14, the porosity of the dentin bridge was determined on Masson's trichrome-stained sections by measuring the percentage of space containing cells within the reparative dentin.

Statistical Analyses

Results are presented as mean±standard error values of independent replicates.

Student's t test was used to quantify differences described in this article. P0.05 was considered to be significant.

Results

When Odontoblasts are Wnt Responsive

Figure 1C:
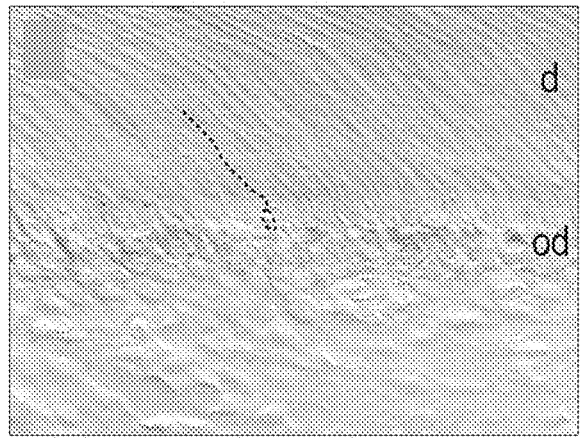
Figure 1D:
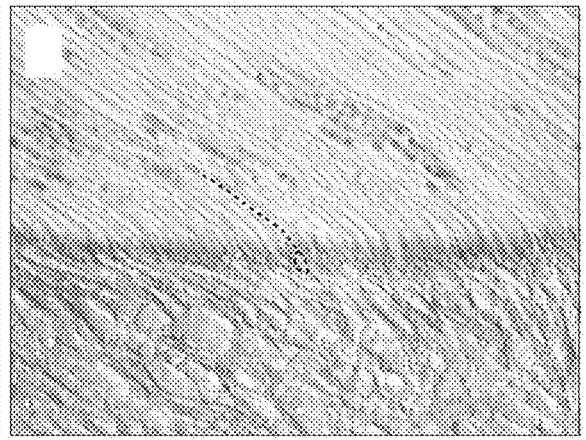
Figure 1E:
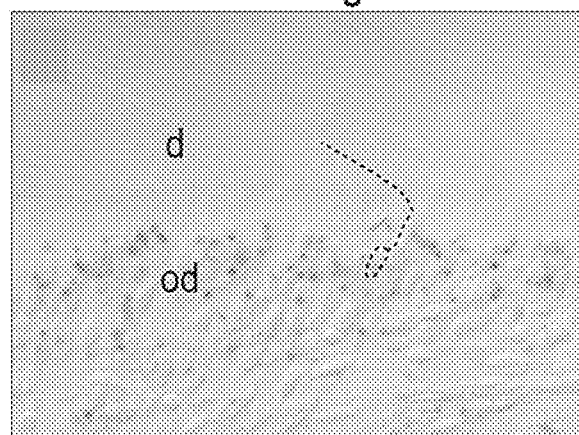
Figure 1F:
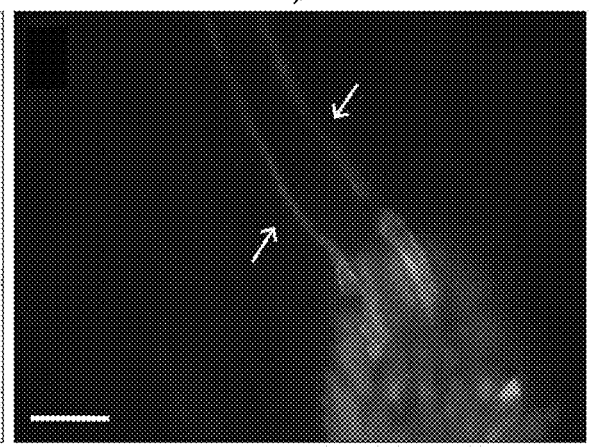

Odontoblasts are distinguished from pulp cells by the expression of the intermediate filament protein Nestin (FIG. 1C (22)), and dentin sialoprotein, DSP (FIG. 1A-D) (23)). Using X-gal staining of tissues from Axin2$^{LacZ/+}$ mice, in which the promoter of the Wnt target gene Axin2 drives LacZ expression (24,25), the odontoblasts lining the inner surface of the pulp cavity were Wnt responsive (FIG. 1E). A second, inducible Axin2 reporter strain (Axin2$^{CreERT2/+}$; R26R$^{mTmG/+}$) verified that odontoblasts respond to an endogenous Wnt signal: GFP immunofluorescence was readily apparent in odontoblast cell bodies and the processes that extended into the dentin (FIG. 1F). Analyses of embryonic and early post-natal dental tissues (FIG. 6) showed that odontoblasts were also Wnt responsive, indicating that these cells maintain a Wnt responsive status throughout their lifetime.

Deletion of Axin2 does not Affect the Dentin/Pulp Complex

Using Axin2$^{LacZ/LacZ}$ mice, in which the negative Wnt regulator Axin2 is deleted (24,25), and Wnt responsiveness is elevated (10,26), the gross morphology of the teeth from Axin2$^{LacZ/+}$ and Axin2$^{LacZ/LacZ}$ mice was evaluated and no significant differences were found in the size of the pulp cavities, or the thickness and density of the alveolar bone, and the size of the pulp chambers was unaffected by Axin2 deletion (FIG. 2A-F). The dentin volume (FIG. 2G), and the mineral densities of enamel and dentin were also equivalent in Axin2$^{LacZ/+}$ and Axin2$^{LacZ/LacZ}$ mice (FIG. 2H). Histologic examination showed that the Axin2$^{LacZ/LacZ}$ pulp was indistinguishable from heterozygous and wild-type littermates (FIG. 2I,J; N≥20 for each genotype). The distribution of X-gal$^{+ve}$ cells in Axin2$^{LacZ/LacZ}$ and Axin2$^{LacZ/+}$ mice was unchanged; the only difference of note was the intensity of X-gal staining in Axin2$^{LacZ/LacZ}$ mice, which is expected since the homozygous mice carry two copies of the LacZ-gene (FIG. 2K, L).

Figure 2P:
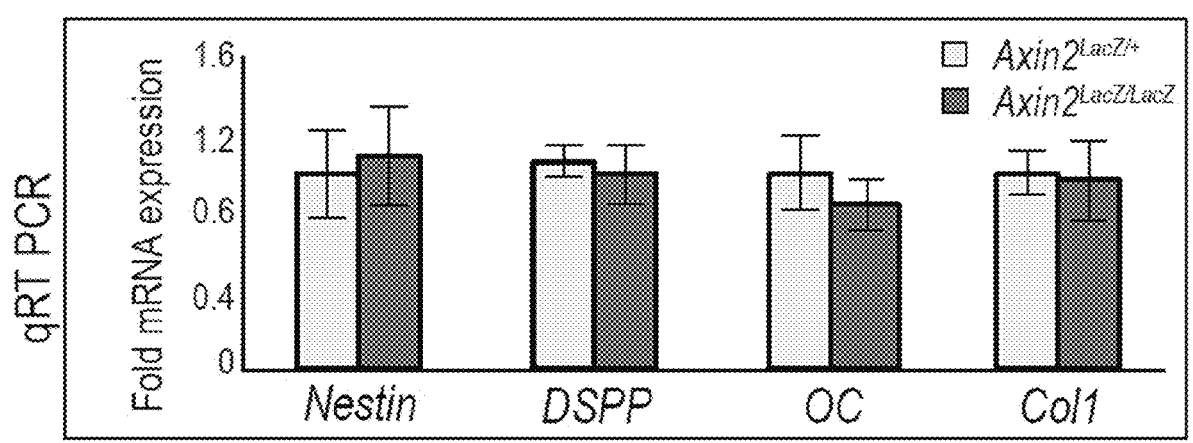

Axin2 is a ligand-dependent inhibitor of Wnt signaling; consequently, it is anticipated that in the absence of a Wnt stimulus Axin2$^{Lac/LacZ}$ mice should show baseline Wnt signaling, equivalent to that seen in Axin2$^{LacZ/+}$ and wild type mice (10,24). Quantitative RT-PCR verified that baseline Wnt signaling, as measured by Lef1 and Axin2 (exon 1) expression was equivalent in Axin2$^{LacZ/+}$ and Axin2$^{LacZ/LacZ}$ mice (FIG. 2M). Markers of cell proliferation (FIG. 2M), and the odontogenic proteins Nestin (FIG. 2N,O), DSPP, Osteocalcin, and Collagen type I (FIG. 2P) showed no significant differences in expression levels between Axin2$^{LacZ/+}$ and Axin2$^{LacZ/LacZ}$ mice.

Axin2$^{LacZ/LacZ}$ Mice Exhibit a Superior Reparative Response Following Acute Pulp Exposure The response of Axin2$^{LacZ/LacZ}$ mice and their Axin2$^{LacZ/+}$ control littermates to an acute pulp exposure was tested. By post-op day 14, the pulp cavities in Axin2$^{LacZ/+}$ mice were largely necrotic (N=6; FIG. 3A). A distinctly different response was observed in Axin2$^{LacZ/LacZ}$ mice, where instead of necrotic pulp tissue the cavity was occupied by reparative dentin (N=6; FIG. 3B; quantified in C). The organization of this matrix was examined using picrosirius red staining and with visualization under polarized light. In Axin2$^{LacZ/+}$ controls, no organized collagenous network was evident in the injury site (FIG. 3D); in contrast, in Axin2$^{LacZ/LacZ}$ mice a dense and packed collagen fiber network forming the bridge was obvious (FIG. 3E). In Axin2$^{LacZ/LacZ}$ mice but not in controls, dentin-secreting cells were immunopositive for DSP (FIG. 3G) and Nestin (FIG. 3I).

Figure 3L:
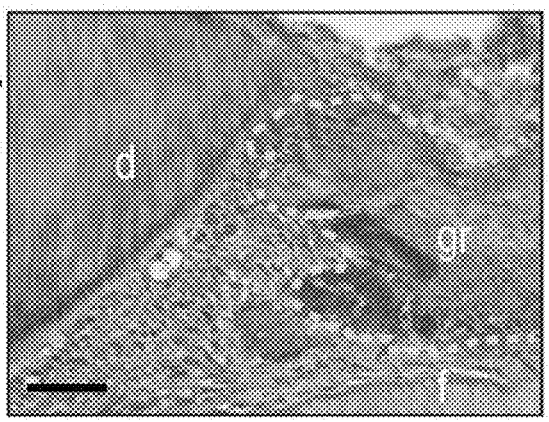
FIG. 3A-3Q. Injury response to an acute pulp exposure in $Axin2^{LacZ/LacZ}$ mice.
(FIG. 3B) In $Axin2^{LacZ/LacZ}$ mice, the pulp injury site is occupied by a green-yellow mineralized matrix and a dense infiltrate of cells.
(FIG. 3C) Quantification of the histomorphometric analyses, demonstrating pulp injury sites in $Axin2^{LacZ/LacZ}$ mice. Under polarized light, Picrosirius red staining of (FIG. 3D) $Axin2^{LacZ/+}$ injury sites and (FIG. 3E) $Axin2^{LacZ/LacZ}$ injury sites. In tissues from $Axin2^{LacZ/+}$ and $Axin2^{LacZ/LacZ}$ mice respectively, immunostaining for (FIG. 3F-3G) DSP, and (FIG. 3H-3I) Nestin. Pentachrome staining of pulp injuries on post-injury day 4 in (FIG. 3J) $Axin2^{LacZ/+}$ and in (FIG. 3K) $Axin2^{LacZ/LacZ}$ mice, quantified in (FIG. 3L) where Axin2 exon1 expression was measured. TUNEL staining indicates programmed cell death in (FIG. 3M) $Axin2^{LacZ/+}$ and (FIG. 3Q) $Axin2^{LacZ/LacZ}$ mice (FIG. 3O) Quantitative RT-PCR for CASP8 expression. On post-injury day 7, Ki67 immunostaining in (FIG. 3P) $Axin2^{LacZ/+}$ and (FIG. 3Q) $Axin2^{LacZ/LacZ}$ mice. Abbreviations: ab, alveolar bone; d, dentin; f, furcation; gr, granulation tissue; p, pulp. Scale bars: 50 µm (FIG. 3K-3L), 100 µm (FIG. 3N-3O), 50 µm (FIG. 3H-3I), 100 µm (FIG. 3A-3B), 100 µm (FIG. 3D-3I), 25 µm (FIG. 3N), and 50 µm (FIG. 3O). Single asterisk denotes P<0.05. Double asterisk denotes P<0.01. Error Bars represent SEM.

On post-op day 4, granulation tissue filled the pulp chambers in Axin2$^{LacZ/+}$ controls (N=6; FIG. 3J). Axin2$^{LacZ/LacZ}$ mice showed minimal granulation tissue (N=6; FIG. 3K). Quantitative RT-PCR revealed that the endogenous Wnt response, as measured by Axin2 exon1 expression, was significantly elevated in Axin2$^{LacZ/LacZ}$ mice compared to controls (FIG. 3L).

Exposure of the pulp causes extensive cellular necrosis (28); there is also a period of latent apoptosis when pulp cells damaged by the injury can either die or recover (29). In Axin2$^{LacZ/+}$ controls, abundant TUNEL staining identified these dying cells (FIG. 3M). In Axin2$^{LacZ/LacZ}$ mice, very few TUNEL$^{+ve}$ cells were evident, even on post-op day 4 (FIG. 3N). Apoptosis is largely controlled by caspase activity (30) and as anticipated by the TUNEL staining, Casp8 expression in Axin2$^{LacZ/LacZ}$ mice was significantly lower than its expression in Axin2$^{LacZ/+}$ controls (FIG. 3O). Cell proliferation, as indicated by Ki67 immunostaining, was greater in Axin2$^{LacZ/LacZ}$ mice compared to Axin2$^{LacZ/+}$ controls (FIG. 3P,Q). Thus, in response to an acute pulp injury that caused a significant elevation in endogenous Wnt signaling, Axin2$^{LacZ/LacZ}$ mice fared better than their heterozygous littermates. The elevated Wnt environment was correlated with reduced cell death, enhanced cell proliferation, and an overall improvement in the repair response of the pulp.

Wnt Signaling Regulates Apoptosis and Proliferation in Dental Pulp Stem Cells

Figure 4A:
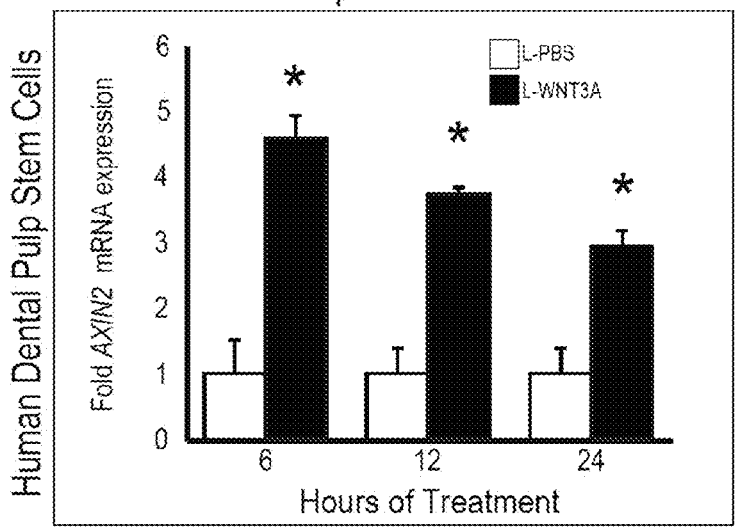
FIG. 4A-4F. WNT3A stimulates proliferation and survival of human dental pulp stem cells and mouse bone marrow-derived stem cells.
Figure 4B:
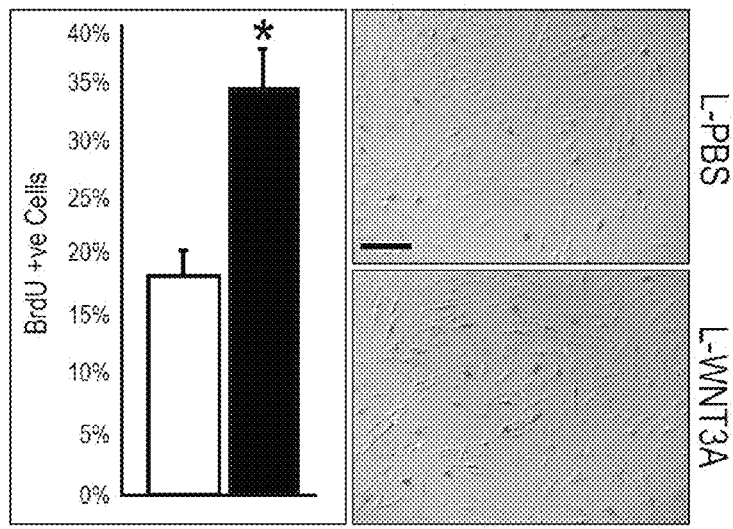
Figure 4C:
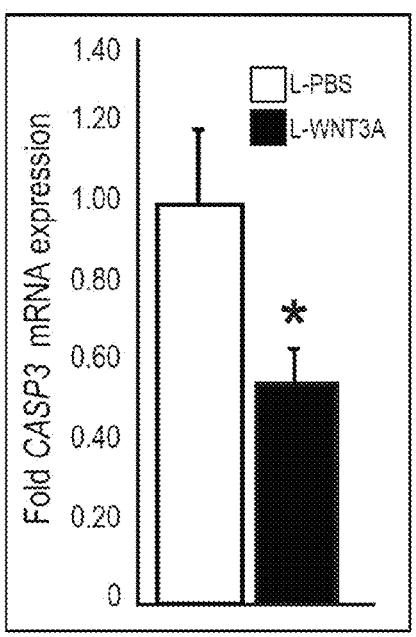

It was tested whether a Wnt stimulus alone was sufficient to reduce cell death and enhance cell proliferation in pulp cells. Dental pulp stem cells were isolated from human teeth (19) and analyzed first for their responsiveness to WNT3A protein (13). Within 6 hours of treatment, dental pulp stem cells exhibited a 4.8-fold increase in Axin2 expression that persisted for at least 24 h (FIG. 4A). The mitotic activity of dental pulp stem cells was significantly increased by L-WNT3A treatment (FIG. 4B). Human CASPASE 3 expression was significantly reduced by L-WNT3A treatment (FIG. 4C).

Figure 4D:
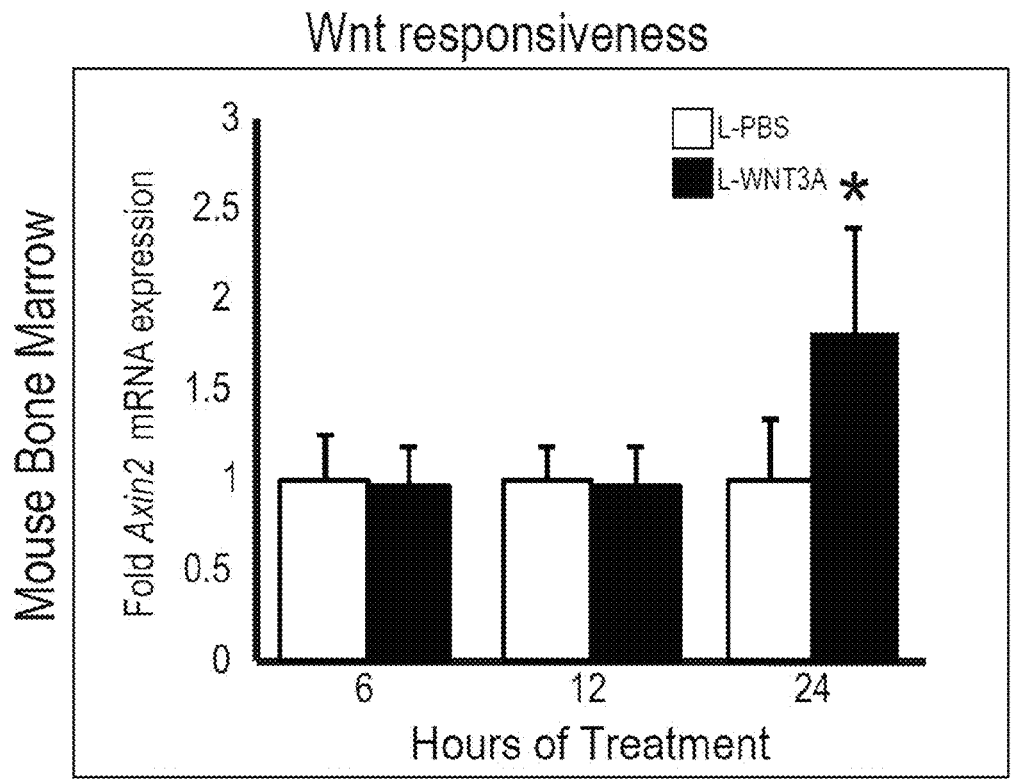
Figure 4E:
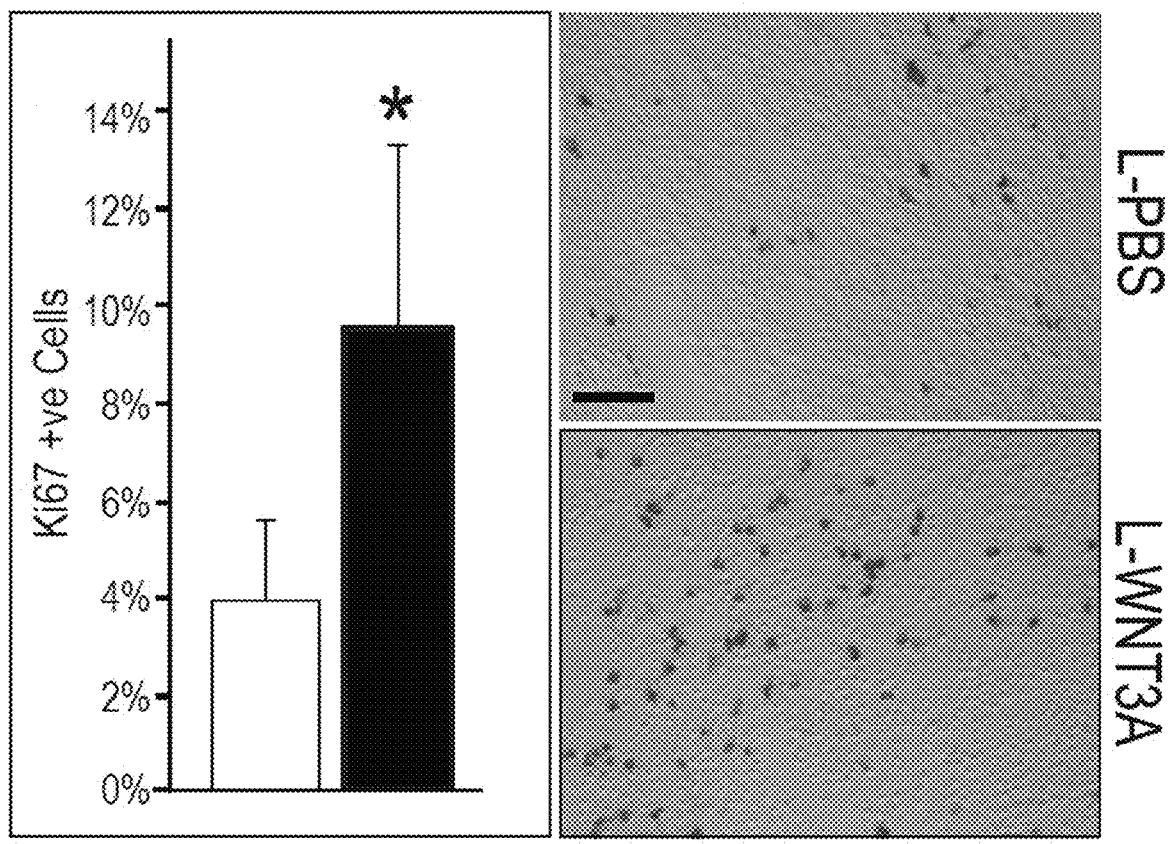
Figure 4F:
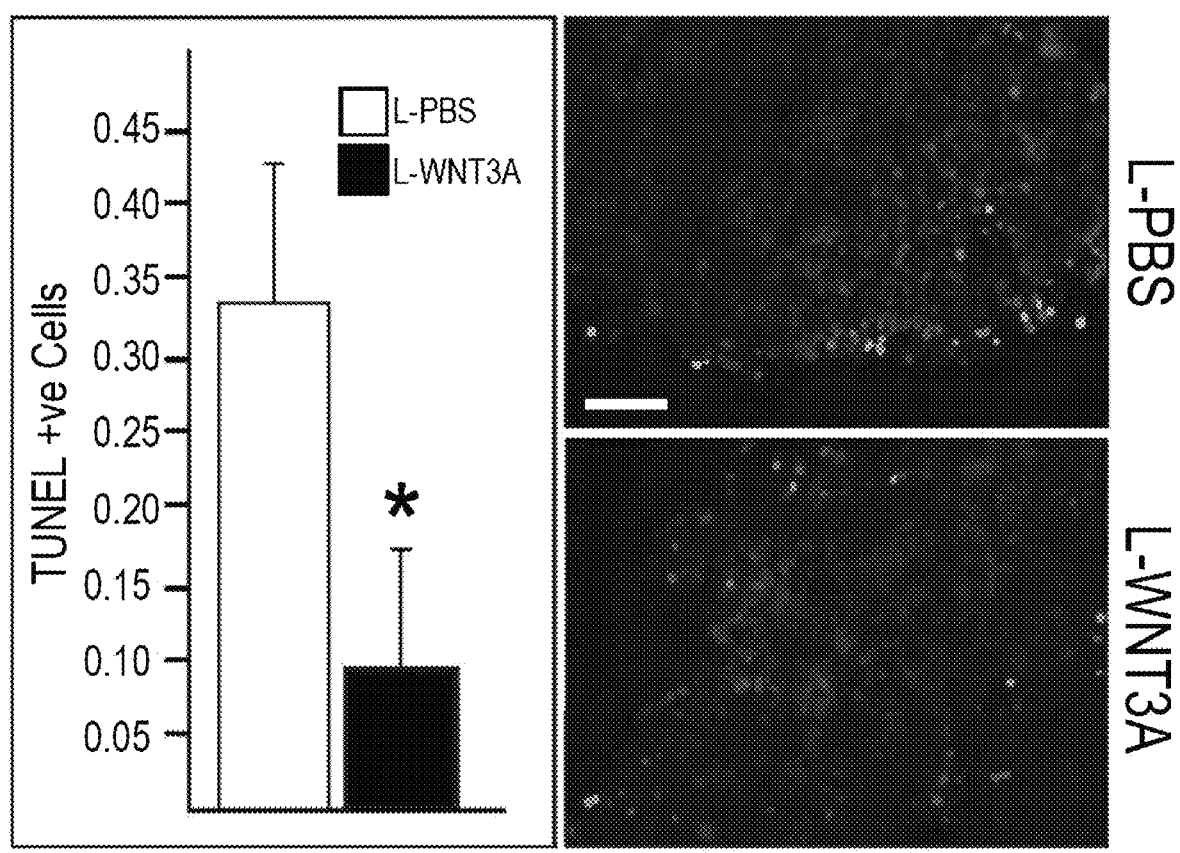

In their undifferentiated state, pulp and bone marrow have been considered equivalent tissues (31,32). Whether freshly harvested bone marrow responded to L-WNT3A in a manner similar to the human dental pulp stem cells was then tested. Whole bone marrow from mice was harvested and treated with L-WNT3A or L-PBS and within 24 h a significant increase in Wnt responsiveness was detected (FIG. 4D). The elevation in Wnt responsiveness occurred simultaneous with an increase in cell proliferation (FIG. 4E) and a reduction in cell death (FIG. 4F). Thus, exposure to a WNT stimulus is sufficient to activate Wnt signaling, enhance mitotic activity, and reduce apoptosis in two stem cell populations.

L-WNT3A Treatment Preserves Pulp Vitality after an Acute Pulp Exposure

Given the ability of L-WNT3A to reduce apoptosis and promote cell proliferation in vitro, it was then tested whether L-WNT3A could elicit similar effects in pulp tissue after an acute injury. Acute pulp exposures were generated in wild-type rats and treated with L-WNT3A or a liposomal formulation of PBS (L-PBS) then sealed to prevent bacterial contamination. Histological analyses verified that the size and extent of the injury was equivalent between the treatment groups (N=6 for both treatment groups; FIG. 5A,B).

By post-op day 4, L-PBS controls exhibited extensive pulp necrosis and apoptosis (N=6, FIG. 5C,C'); in L-WNT3A treated cases, TUNEL staining was minimal (N=6; FIG. 5D). The TUNEL staining that was observed in the L-WNT3A treated samples was generally restricted to the roof of the pulp cavity, near to the site of exposure (N=6; FIG. 5D').

In an elevated Wnt environment such as is observed in Axin2$^{LacZ/LacZ}$ mice, cell proliferation is significantly elevated after an injury (FIG. 3); this suggests a more vigorous repair response. The same effect following L-WNT3A treatment of the injured pulp was observed: relative to L-PBS treated pulp exposures, proliferating cell nuclear antigen (PCNA) immunostaining was much more extensive in the L-WNT3A treated samples (compare FIG. 5E,F).

Reduced apoptosis and increased proliferation in the L-WNT3A treated pulps culminated in a superior repair response. In L-PBS cases, the pulp was largely occupied on post-op day 14 by a amorphous, bone-like tissue, called atubular osteodentin ((33); FIG. 5G) whereas in L-WNT3A treated cases the pulp cavities were filled with a highly organized, tubular dentin matrix (FIG. 5H). Similar to previous quantitative analyses (FIG. 3C) the dentin appeared to be denser in the L-WNT3A treated samples compared to the L-PBS controls (FIG. 5I).

The reparative dentin matrix, as visualized by picrosirius red staining and polarized light, was distinctly different between the two groups: in L-PBS samples the collagenous matrix exhibited a basket-weaved pattern, characteristic of bone (FIG. 5J); in L-WNT3A samples, the collagenous matrix had a linear organization, suggestive of tubular orthodentin (FIG. 5K).

Differentiated odontoblasts express Nestin (34); few Nestin$^{+ve}$ cells were detected in L-PBS treated samples compared to the L-WNT3A samples (FIG. 5L,M). Differentiated odontoblasts also express the extracellular matrix protein DSP (23) and DSP$^{+ve}$ cells were largely absent from the L-PBS treated pulp compared to the L-WNT3A treated pulp (FIG. 5N,O).

DISCUSSION

When confronted with noxious stimuli the human pulp is capable of mounting a robust repair response—at least in young patients (35,36). In older individuals, the pulp responds to the same noxious stimuli by undergoing necrosis (35).

Previous reports indicated that after postnatal day 15, molar odontoblasts and odontoblasts at the incisor tip lose their Wnt responsiveness (44). The question of whether polarized, secretory odontoblasts maintain their dependence upon a Wnt signal into adulthood was addressed herein. Two separate approaches were used: first, cryo-sectioned tissues from adult Axin2$^{LacZ/+}$ Wnt reporter mice were analyzed and both polarized odontoblasts and pulp cells were found to be X-gal$^{+ve}$ (FIG. 1E, and FIG. 2K). Second, tissues from adult Axin2$^{CreERT2/+}$; R26R$^{mTmG/+}$ Wnt reporter mice also illustrated that polarized odontoblasts were GFP$^{+ve}$ (FIG. 1F). Thus, adult odontoblasts and pulp cells maintain a Wnt responsive status in adulthood.

In the absence of a Wnt stimulus Axin2$^{LacZ/LacZ}$ cells behave the same as wild-type cells (10). Because Axin2 represses Wnt signaling in a ligand-dependent manner (24, 25), the removal of Axin2 results in an amplified Wnt response (10,24). The response to pulpal injury can be enhanced by elevating Wnt signaling by either removing a negative Wnt regulator (FIG. 3), or by providing exogenous WNT3A protein (FIG. 5), which is sufficient to significantly improve the pulp cavity's repair response.

The mechanism of WNT action in the pulp may be due in part to the response of stem/progenitor cells within this tissue. Human dental pulp stem cells responded to human WNT3A protein by strongly up activating the Wnt pathway, by becoming mitotically active, and by down-regulating caspase activity (FIGS. 4,5), an enzyme that mediates the execution phase of apoptosis (50). Collectively, these biological responses are valuable in therapeutic strategies that seek to improve a healing response.

In addition to these biological responses, a difference was noted in the type of reparative mineralized tissue that formed after L-PBS and L-WNT3A treatment (FIG. 5). In L-PBS treated samples, a bone-like mineralized matrix, osteodentin, forms. Compared to dentin, osteodentin is porous and consequently its appearance in the injured pulp represents a sub-optimal healing response. In L-WNT3A cases the reparative matrix resembled native dentin (FIG. 5H,K). This dentin matrix was produced by native DSP$^{+ve}$ secretory odontoblasts (FIG. 5M) and it formed a dentin bridge that effectively separated the viable pulp cavity from the external environment. No such dentin bridge was evident in controls.

Figure 3L:
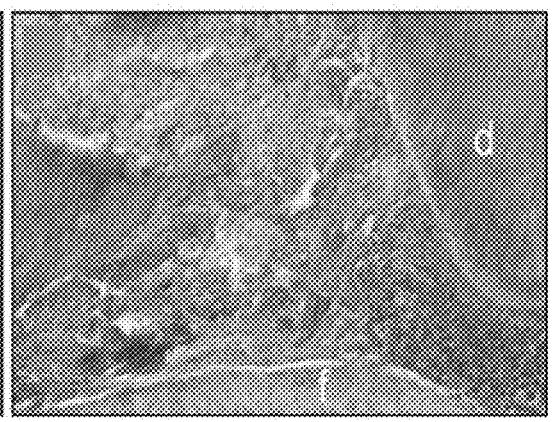
Figure 3L:
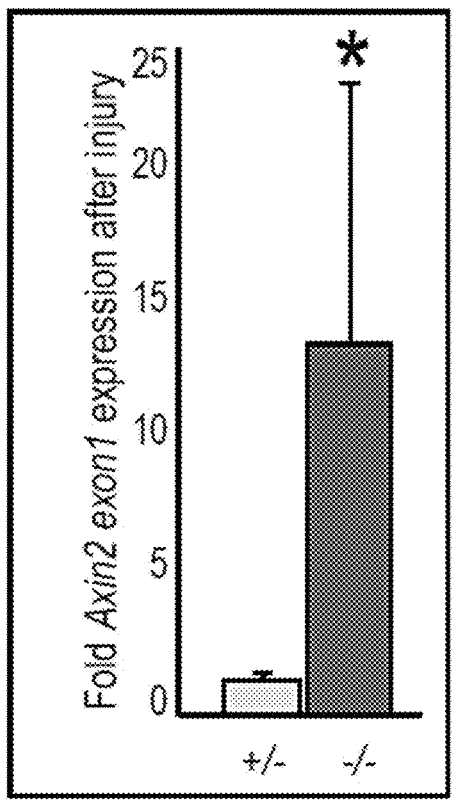

The present disclosure provides an approach (e.g., to root canal therapy) that exploits the reliance of pulp cells on endogenous Wnt signaling (FIGS. 3,4). A liposome-reconstituted form of WNT3A protein effectively protected pulp cells from death and stimulated proliferation of undifferentiated cells in the pulp, which together significantly improved pulp healing. The strategy of activating endogenous stem cells via L-WNT3A to improve healing represents a viable means to achieving pulp regeneration in humans.

REFERENCES

1. Love R M, Jenkinson H F 2002 Invasion of dentinal tubules by oral bacteria. Crit Rev Oral Biol Med 13(2): 171-83.
2. Herman B 1928 Ein weiterer Beitrag zur Frage der Pulpenbehandlung. Zahnarztliche Rundschau 37). :1327-76.
3. Goldberg M, Farges J C, Lacerda-Pinheiro S, Six N, Jegat N, Decup F, Septier D, Carrouel F, Durand S, Chaussain-Miller C, Denbesten P, Veis A, Poliard A 2008 Inflammatory and immunological aspects of dental pulp repair. Pharmacol Res 58(2):137-47.
4. Chen S, Gluhak-Heinrich J, Wang Y H, Wu Y M, Chuang H H, Chen L, Yuan G H, Dong J, Gay I, MacDougall M 2009 Runx2, osx, and dspp in tooth development. J Dent Res 88(10):904-9.
5. Komori T 2010 Regulation of bone development and extracellular matrix protein genes by RUNX2. *Cell* Tissue Res 339(1):189-95.
6. Sognnaes R F 1959 Dentistry at its centennial crossroads. Science 130(3390):1681-8.
7. Arany P R, Cho A, Hunt T D, Sidhu G, Shin K, Hahm E, Huang G X, Weaver J, Chen A C, Padwa B L, Hamblin M R, Barcellos-Hoff M H, Kulkarni A B, D J M 2014 Photoactivation of endogenous latent transforming growth factor-beta1 directs dental stem cell differentiation for regeneration. Sci Transl Med 6(238):238ra69.
8. Huang G T 2011 Dental pulp and dentin tissue engineering and regeneration: advancement and challenge. Front Biosci (Elite Ed) 3:788-800.
9. Thesleff I, Tummers M 2008 Tooth organogenesis and regeneration StemBook, Cambridge (Mass.).
10. Minear S, Leucht P, Jiang J, Liu B, Zeng A, Fuerer C, Nusse R, Helms J A 2010 Wnt proteins promote bone regeneration. Sci Transl Med 2(29):29ra30.
11. Westendorf J J, Kahler R A, Schroeder T M 2004 Wnt signaling in osteoblasts and bone diseases. Gene 341:19-39.
12. Moon R T, Kohn A D, De Ferrari G V, Kaykas A 2004 WNT and beta-catenin signalling: diseases and therapies. Nat Rev Genet 5(9):691-701.
13. Dhamdhere G R, Fang M Y, Jiang J, Lee K, Cheng D, Olveda R C, Liu B, Mulligan K A, Carlson J C, Ransom R C, Weis W I, Helms J A 2014 Drugging a stem cell compartment using Wnt3a protein as a therapeutic. PLoS One 9(1):e83650.
14. Zhao L, Rooker S M, Morrell N, Leucht P, Simanovskii D, Helms J A 2009 Controlling the in vivo activity of Wnt liposomes. Methods Enzymol 465:331-47.
15. Salmon B, Bardet C, Khaddam M, Naji J, Coyac B R, Baroukh B, Letourneur F, Lesieur J, Decup F, Le Denmat D, Nicoletti A, Poliard A, Rowe P S, Huet E, Vital S O, Linglart A, McKee M D, Chaussain C 2013 MEPE-derived ASARM peptide inhibits odontogenic differentiation of dental pulp stem cells and impairs mineralization in tooth models of X-linked hypophosphatemia. PLoS ONE 8(2):e56749.
16. Lim W H, Liu B, Cheng D, Hunter D J, Zhong Z, Ramos D M, Williams B O, Sharpe P T, Bardet C, Mah S J, Helms J A 2013 Wnt signaling regulates pulp volume and dentin thickness. J Bone Miner Res.
17. Minear S, Leucht P, Miller S, Helms J A 2010 rBMP represses Wnt signaling and influences skeletal progenitor cell fate specification during bone repair. J Bone Miner Res 25(6):1196-207.

18. Brugmann S A, Goodnough L H, Gregorieff A, Leucht P, ten Berge D, Fuerer C, Clevers H, Nusse R, Helms J A 2007 Wnt signaling mediates regional specification in the vertebrate face. Development 134(18):3283-95.
19. Khanna-Jain R, Mannerstrom B, Vuorinen A, Sandor G K, Suuronen R, Miettinen S 2012 Osteogenic differentiation of human dental pulp stem cells on beta-tricalcium phosphate/poly (l-lactic acid/caprolactone) three-dimensional scaffolds. J Tissue Eng 3(1):2041731412467998.
20. Leucht P, Jiang J, Cheng D, Liu B, Dhamdhere G, Fang M Y, Monica S D, Urena J J, Cole W, Smith L R, Castillo A B, Longaker M T, Helms J A 2013 Wnt3a reestablishes osteogenic capacity to bone grafts from aged animals. J Bone Joint Surg Am 95(14):1278-88.
21. Bataille C, Mauprivez C, Hay E, Baroukh B, Brun A, Chaussain C, Marie P J, Saffar J L, Cherruau M 2012 Different sympathetic pathways control the metabolism of distinct bone envelopes. Bone 50(5):1162-72.
22. Farahani R M, Simonian M, Hunter N 2011 Blueprint of an ancestral neurosensory organ revealed in glial networks in human dental pulp. J Comp Neurol 519(16): 3306-26.
23. Begue-Kirn C, Krebsbach P H, Bartlett J D, Butler W T 1998 Dentin sialoprotein, dentin phosphoprotein, enamelysin and ameloblastin: tooth-specific molecules that are distinctively expressed during murine dental differentiation. Eur J Oral Sci 106(5):963-70.
24. Lustig B, Jerchow B, Sachs M, Weiler S, Pietsch T, Karsten U, van de Wetering M, Clevers H, Schlag P M, Birchmeier W, Behrens J 2002 Negative feedback loop of Wnt signaling through upregulation of conductin/axin2 in colorectal and liver tumors. Mol *Cell* Biol 22(4):1184-93.
25. Jho E H, Zhang T, Domon C, Joo C K, Freund J N, Costantini F 2002 Wnt/beta-catenin/Tcf signaling induces the transcription of Axin2, a negative regulator of the signaling pathway. Mol *Cell* Biol 22(4):1172-83.
26. Liu B, Hunter D J, Rooker S, Chan A, Paulus Y M, Leucht P, Nusse Y, Nomoto H, Helms J A 2013 Wnt signaling promotes Muller cell proliferation and survival after injury. Invest Ophthalmol Vis Sci 54(1):444-53.
27. Fancy S P, Harrington E P, Yuen T J, Silbereis J C, Zhao C, Baranzini S E, Bruce C C, Otero J J, Huang E J, Nusse R, Franklin R J, Rowitch D H 2011 Axin2 as regulatory and therapeutic target in newborn brain injury and remyelination. Nat Neurosci 14(8):1009-16.
28. Stanley H R, Weisman M I, Michanowicz A E, Bellizzi R 1978 Ischemic infarction of the pulp: sequential degenerative changes of the pulp after traumatic injury. J Endod 4(11):325-35.
29. Baume L J 1980 The biology of pulp and dentine. In: Myers H M (ed.) Monographs in Oral Science, vol. 8. Karger, Basel, Switzerland.
30. Cohen G M 1997 Caspases: the executioners of apoptosis. Biochem J 326 (Pt 1):1-16.
31. Shi S, Gronthos S 2003 Perivascular niche of postnatal mesenchymal stem cells in human bone marrow and dental pulp. J Bone Miner Res 18(4):696-704.
32. Shi S, Robey P G, Gronthos S 2001 Comparison of human dental pulp and bone marrow stromal stem cells by cDNA microarray analysis. Bone 29(6):532-9.
33. Goldberg M, Kulkarni A B, Young M, Boskey A 2011 Dentin: structure, composition and mineralization. Front Biosci (Elite Ed) 3:711-35.
34. Fujita S, Hideshima K, Ikeda T 2006 Nestin expression in odontoblasts and odontogenic ectomesenchymal tissue of odontogenic tumours. J Clin Pathol 59(3):240-5.
35. Lin L M, Ricucci D, Huang G T 2013 Regeneration of the dentine-pulp complex with revitalization/revascularization therapy: challenges and hopes. Int Endod J.
36. Murray P E, About I, Lumley P J, Franquin J C, Windsor L J, Smith A J 2003 Odontoblast morphology and dental repair. J Dent 31(1):75-82.
37. Miura M, Gronthos S, Zhao M, Lu B, Fisher L W, Robey P G, Shi S 2003 SHED: stem cells from human exfoliated deciduous teeth. Proc Natl Acad Sci USA 100(10):5807-12.
38. Ruch J V 1987 Determinisms of odontogenesis. Revis Biol Celular 14:1-99.
39. Smith A J, Cassidy N, Perry H, Begue-Kirn C, Ruch J V, Lesot H 1995 Reactionary dentinogenesis. Int J Dev Biol 39(1):273-80.
40. Smith A J, Lesot H 2001 Induction and regulation of crown dentinogenesis: embryonic events as a template for dental tissue repair? Crit Rev Oral Biol Med 12(5):425-37.
41. Goldberg M 2011 Pulp healing and regeneration: more questions than answers. Adv Dent Res 23(3):270-4.
42. Goldberg M, Six N, Chaussain C, DenBesten P, Veis A, Poliard A 2009 Dentin extracellular matrix molecules implanted into exposed pulps generate reparative dentin: a novel strategy in regenerative dentistry. J Dent Res 88(5):396-9.
43. Tziafas D 2004 The future role of a molecular approach to pulp-dentinal regeneration. Caries Res 38(3):314-20.
44. Lohi M, Tucker A S, Sharpe P T 2010 Expression of Axin2 indicates a role for canonical Wnt signaling in development of the crown and root during pre- and postnatal tooth development. Dev Dyn 239(1):160-7.
45. Seifert A W, Kiama S G, Seifert M G, Goheen J R, Palmer T M, Maden M 2012 Skin shedding and tissue regeneration in African spiny mice (Acomys). Nature 489:561-5.
46. Stoick-Cooper C L, Moon R T, Weidinger G 2007 Advances in signaling in vertebrate regeneration as a prelude to regenerative medicine. Genes Dev 21(11): 1292-315.
47. Beers M F, Morrisey E E 2011 The three R's of lung health and disease: repair, remodeling, and regeneration. J Clin Invest 121(6):2065-73.
48. Duan J, Gherghe C, Liu D, Hamlett E, Srikantha L, Rodgers L, Regan J N, Rojas M, Willis M, Leask A, Majesky M, Deb A 2012 Wnt1/betacatenin injury response activates the epicardium and cardiac fibroblasts to promote cardiac repair. EMBO J 31(2):429-42.
49. Whyte J, Smith A, Liu B, Manzano W R, Evans N D, Dhamdhere G, Fang M, Chang H Y, Oro A E, Helms J A 2013 Augmenting endogenous Wnt signaling improves skin wound healing PLoS ONE In press.
50. Chowdhury I, Tharakan B, Bhat G K 2008 Caspases—an update. Comp Biochem Physiol B Biochem Mol Biol 151(1):10-27.

Example 2

The example provided herein demonstrates penetration of L-Wnt3A through dentinal tubules and activation of pulp cells.

Rodent dentinal tubules and human dentinal tubules have similar diameters.

Therefore, a rodent model was used to demonstrate penetration of the L-WNT3A through the dentinal tubules to the pulp (FIG. 8). Topical application of the liposomal mixture penetrates the dentinal tubules. In a Wnt reporter Axin2CreERT2/+; R26RmTmG/+ mouse strain, the delivery of the hydrophobic tamoxifen molecule, in association with the same liposome used to package WNT3A, results in Cre-mediated recombination event in pulp cells located immediately beneath the cavity preparation. L-WNT3A exposure acts as a survival signal for odontoblasts. Typically after exposure to a toxic (e.g., heat, chemical) agent, most odontoblasts die; this eventually necessitates the removal of the necrotic pulp and its replacement with an inert filling material, through a process known as a root canal. *Cell* death is significantly decreased provided odontoblasts are exposed to the pro-survival signal L-WNT3A.

Liposomes were fabricated from dimyristoyl-phosphatidylcholine lipids. Liposomes were made with tamoxifen and used in combination with a tamoxifen inducible mouse strain Axin2CreERT2/+; R26RmTmG/+ and their penetration were monitored over the course of 14 d. The liposomes were effective at penetrating to the cells below the deep cavity preparation and inducing genetic recombination of the cell. The ability of L-WNT3A to stimulate proliferation in dental pulp stem and progenitor cells, and in odontoblasts was demonstrated above. The ability of L-WNT3A to curtail programmed cell death through a caspase 8-mediated mechanism was demonstrated above. The ability of L-WNT3A to enhance expression of molecules associated with dentin secretion including dentin sialoprotein (DSP) and Nestin has also been demonstrated herein.

What is claimed:

1. A method for enhancing dentin production, the method comprising:
    (a) providing a tissue from a subject;
    (b) contacting the tissue with liposomal Wnt3A, wherein the liposomal Wnt3A comprises a Wnt3A protein inserted into a non-aqueous phase of a lipid structure, thereby forming a Wnt3A-modified tissue; and
    (c) administering the Wnt3A-modified tissue to a tooth of the subject.

2. The method according to claim 1, wherein the Wnt3A protein is human Wnt3A.

3. The method according to claim 1, wherein the Wnt3A protein has an amino acid sequence of SEQ ID NO: 19.

4. The method according to claim 1, wherein the lipid structure comprises a size range of from 0.03 to 0.2 micron.

5. The method according to claim 1, wherein the tissue is derived from dental pulp.

6. The method according to claim 1, wherein the tissue is derived from bone marrow.

7. The method according to claim 1, wherein the tissue provided from the subject is from the tooth to which the Wnt3A-modified tissue is administered.

8. The method according to claim 1, wherein the tissue provided from the subject is from a different tooth of the subject than that to which the Wnt3A-modified tissue is administered.

9. The method according to claim 1, wherein the Wnt3A-modified tissue is present in an amount sufficient to activate stem cells, progenitor cells, or a combination thereof in the tissue.

10. The method according to claim 1, wherein the Wnt3A-modified tissue is present in an amount sufficient to reduce apoptosis of a dental pulp tissue in the tooth of the subject.

11. The method according to claim 1, wherein the Wnt3A-modified tissue is administered to dental pulp tissue within the tooth.

12. The method according to claim 1, wherein administering the Wnt3A-modified tissue increases the number of differentiated odontoblasts in the tooth.

13. The method according to claim 1, wherein the Wnt3A-modified tissue promotes secretion of dentin matrix from odontoblasts in the tooth.

14. The method according to claim 1, wherein the Wnt3A-modified tissue further comprises a pharmaceutically acceptable carrier.

15. The method according to claim 1, wherein the Wnt3A-modified tissue is administered as a single administration.

16. The method according to claim 1, wherein the Wnt3A-modified tissue is administered as part of a series of administrations.

17. The method according to claim 1, wherein the subject is a human.

18. The method according to claim 1, wherein the method is performed as part of a dental procedure.

19. The method according to claim 18, wherein the dental procedure is a deep dental restoration.

20. The method according to claim 19, wherein the deep dental restoration comprises placement of an amalgam, composite, or crown within the tooth.

* * * * *

UNITED STATES PATENT AND TRADEMARK OFFICE
CERTIFICATE OF CORRECTION

| | |
|---|---|
| PATENT NO. | : 11,260,103 B2 |
| APPLICATION NO. | : 16/669340 |
| DATED | : March 1, 2022 |
| INVENTOR(S) | : Helms et al. |

It is certified that error appears in the above-identified patent and that said Letters Patent is hereby corrected as shown below:

On the Title Page

Item (72) Inventor is corrected to read:
--Jill Helms, Sanford, CA (US);
Daniel J. Hunter, Stanford, CA (US)--.

Signed and Sealed this
Fifth Day of August, 2025

Coke Morgan Stewart
*Acting Director of the United States Patent and Trademark Office*